United States Patent [19]
McKay et al.

[11] Patent Number: 5,338,839
[45] Date of Patent: Aug. 16, 1994

[54] DNA ENCODING NESTIN PROTEIN

[75] Inventors: Ronald D. G. McKay, Brookline, Mass.; Urban Lendahl, Stockholm, Sweden

[73] Assignee: Massachusetts Institute of Technology, Cambridge, Mass.

[21] Appl. No.: 853,913

[22] Filed: Mar. 19, 1992

Related U.S. Application Data

[63] Continuation-in-part of Ser. No. 660,412, Feb. 22, 1991, abandoned, which is a continuation-in-part of Ser. No. 603,803, Oct. 25, 1990, abandoned, which is a continuation-in-part of Ser. No. 201,762, Jun. 2, 1988, abandoned, which is a continuation-in-part of Ser. No. 180,548, Apr. 12, 1988, abandoned.

[51] Int. Cl.$^5$ .................. C07H 21/04; C12Q 1/68
[52] U.S. Cl. .................. 536/235; 536/24.31; 435/6; 435/912; 935/9; 935/11; 935/78
[58] Field of Search ............ 435/6, 91; 536/27, 23.5, 536/24.31, 24.33; 935/77, 78; 485/91.2

[56] References Cited

FOREIGN PATENT DOCUMENTS

WO89/03872  5/1989  PCT Int'l Appl. .

OTHER PUBLICATIONS

Lendahl, U., et al., "CNS Stem Cells Express a New Class of Intermediate Filament Protein", Cell, 60:585–595 (Feb. 23, 1990).
McKay, R. D., "A cerebeller stem cell model for meduiloblastona" (Abstr. 10.30.08) Cancer Research & Clinical Oncology, 116 (1990).
Zimmerman et al., "Molecular Cloning of Nestin: A Novel Intermediate Filament Restriction to CNS Stem Cells" (Abst. B121); Cancer Research and Clinical Oncology 116 (1990).
McKay R. D., et al., "Molecular cloning of nestin: a novel intermediate filament restricted to CNS stem cells", J. Cell. Biochem. Suppl., p. 223 (1990).
Jat., P. S., et al., "Large T. Antigens of Simian Virus 40 and Polymavirus Efficiently Establish Primary Fibroblasts", J. of Virol. 59(3):746–750 (1986).
Chou, J. Y., "Establishment of Rat Fetal Liver Lines and Characterization of Their Metabolic and Hormonal Properties: Use of Temperature–Sensitive SV40 Virus", Methods in Enzym. 109:385–395 (1985).
Jat, P. S., et al., "Recombinant Retroviruses Encoding Simian Virus 40 Large T Antigen & Polyomavirus Large & Middle T Antigens", Mol. & Cell. Biol. 6(4):1204–1217 (1986).
Hockfield, S., et al., "Identification of Major Cell Classes in the Developing Mammalian Nervous System", J. of Neuroscience 5(12):3310–3328 (1985).
Frederiksen, K., et al., "Proliferation & Differentiation of Rat Neuroepithelial Precursor Cells in vivo", J. of Neuroscience Annl. 8(4):1155–1151 (1988).
Jat, P. S., et al., "Cell Lines Established by a Temperature–Sensitive Simian Virus 40 Large–T–Antigen Gene are Growth Restricted at the Nonpermissive Temperature", Mol. & Cell. Biol. 9(4):1672–1681 (1989).
Frederiksen, K., et al., "Immortalization of Precursor Cells from the Mammalian CNS", Neuron 1:439–448 (1988).
Watanabe, T., et al., "Rod Photoreceptor Development In Vitro: Intrinsic Properties of Proliferating Neuroepithelial Cells Change as Development Proceeds in the Rat Retina", Neuron 4:461–467 (1990).
Reh, T. A., et al., "Age of Differentiation Determines Rat Retinal Germinal Cell Phenotype: Induction of Differentiation by Dissociation" J. of Neuroscience 9(12):4179–4189 (1989).
Temple, S., et al., "Clonal Analysis of Oligodendrocyte (List continued on next page.)

*Primary Examiner*—Margaret Parr
*Assistant Examiner*—Carla Myers
*Attorney, Agent, or Firm*—Hamilton, Brook, Smith & Reynolds

[57] ABSTRACT

A gene (SEQ ID NO: 1 or SEQ ID NO: 3) encoding a protein, nestin, whose expression distinguishes neural multipotential stem cells and brain tumor cells from the more differentiated neural cell types (e.g., neuronal, glial and muscle cells).

5 Claims, 15 Drawing Sheets

OTHER PUBLICATIONS

Development in Culture: Evidence for a Developmental Clock that Counts Cell Divisions". Cell 44:773–779 (1986).

International Search Report; Patent Cooperation Treaty Search Report PCTUS92101375.

Petit, C. A., et al., "Immortalization of Rodent Embryo Fibroblasts by SV40 is Maintained by the A Gene", Virology 127:74–82 (1983).

Beug, H., et al., "Hormone-Dependent Terminal Differentiation in Vitro of Chicken Erythroleukemia Cells Transformed by ts Mutants of Avian Erythroblastosis Virus", Cell 28:907–919 (1982).

Frederiksen, K., et al., "Immortalization of Precursor Cells from the Mammalian CNS", Neuron 1:439–448 (1988).

Lendahl, U., et al., "CNS Stem cells express a new class of Intermediate filament protein", Cell 60:585–595 (1990).

Valtz, N. L. M., et al., "An Embryonic Origin for Medulloblastoma" The New Biologist, 3(4):364–371 (1991).

Redies, C., et al., "Differentiation and Heterogeneity in T-Antigen Immortalized Precursor Cell Lines From Mouse Cerebellum", J. of Neurosci. Res., 30:601–615 (1991).

Tohyama, T., et al., "Nestin Expression in Embryonic Human Neuroepithelium and in Human Neuroepithelial Tumor Cells", Laboratory Investigation 66(3):303–313 (1992).

Figure 1A

```
   1  CGTGTTTGCT TTAGCAAGAC GTCTTTTTAC CTGTGTACCC CAAAAAACAT
  51  CATTTGATGT AACTAACTTA CTCAAGGCTA TTGAGCCAGA GGGGXAAATT
 101  CAGAGCCACC AXXXXGTGCA AGGCACAGTG CCATAAGGGT CATAGTCAAG
 151  CACTTGCAGT CTCTTTAGAA CATGGTCGGT GCTXCAGAGA AGGATAGAGA
 201  AAAGGAAAGA TACCCTCTTT GCCCXGGAGA CCTCCGXGCX XGXGGAAAAT
 251  TTATATGATC CACAGTAGTG GGTATGTAAC AGGCATACAA GCCAAACACT
 301  GATAGTCATA AAGACATTCA TGTTAGAACA AATTCTTGGT ATACAGATTA
 351  TTTTTCCATT TTTAAAAGAT GAAAGAAGCT TTTCCTGCTA ATGGGAAGGA
 401  TCGCTTGTTT ATCCTCACGT AGCATTGAAT GTTCTTGGCT GAACATTTGG
 451  TATTTAAAAC CATGGTAGAA CATCTTCAAC GTTTTCAGAA TTGATCCATA
 501  CTTTGATTTA AAAAGTAGTT TATTGGGTTG GGATTTAGCT CAGTGGTAGA
 551  GGCTTGCCTG AAGCCAAGGC CTGGTTCGTC CCACGACGTC TCGCAGAAAA
 601  AAGAGAAAAG AAAAAGTAGT TTATTGCTAT TTCTGTGTGT GTGTGTGTGT
 651  GTGTGTGTGT GTGTGTGTGT GTGTGTCTGT GTATGTCTGT GCATGGGCAG
 701  TATACCTGTG TGTGGATGCA CATAGAGGTC AGAGGCCTTT GATGTCCCTG
 751  GAGCTGATAT GGGTGCTGAG AATTGTACTT GGGTCTCCGG GAGAGCAGCA
 801  AGTGCTTTTG ACGACTTAGC ATCTCTCCAG CTCAGATATC CTGATTTTCT
 851  AACTGTCAAT GCTGGGAATG CCAATCTGTA TGAATGATTC TGCCCACAGC
 901  AGAAGTATGT TTAGGACCAT TTCAGAAATT GTTGGAAATT TTGTCCTAAT
 951  CGTAAGCCAA AATTCACTGA AGGATTTTAT TTTTCGTTTG AGACAGGATC
1001  TTACTATGTA ATCCTGGCTG GCCTGGAACT CATTTGCTAT GTAGAGGCTG
1051  GCCTTAAACT CAGAGATTGG CATTATTCTG TCTCTTGAGT GCTGGGATTA
1101  AAGGAATTAA ACTGGCCTCA CTGAACGAGG TTTGATGACA CTCAAGTTÀT
1151  CGACTCAAAC AGCTATTTAA AAGAATTTAG ATTTATTACT GTTGTTATTG
1201  TTGTTAGTCT GTGTGTGTGT GTGTGCGCGC GAGCGCAGGT GCACCATGCT
1251  ACAGTATGCC ATGTGCGAGT CAGTTCTCTC CTCACTATGT GGGTCCTGAA
1301  CATCATGGGA GGGAGCTTGG CAACAGGCAC TACCGGCACT GAGCAGCGAC
1351  TCAGAGCTCA CATCTCAATC CACTAGCACA AGGCAGAGAA GGAGCTACTG
```

Figure 1B

```
1401  CAACCTCTCT CAAAGCCTAC CCCCAGTGAT ACACCTCCTC CAACAAGGCC
1451  ATTCCTCCCA ATCCTTCTAA AATAGGTTCT CCAACTGGGG ACCAAGCATT
1501  CAAACATTTA AGCCTAAGGG TCCCTTGTAC AAAGTCCACA ACTTCATTTC
1551  TTTCTTCGCC AGACTGCATC GTTAGCCACC AGGGGGCTCC CCTGAGAGCC
1601  GCGTAGCTTT CTAACTGAGT AAACTGCAAG AGTGTACGAA CAACAAAGGA
1651  GAAAAACTTT CTTGAACGTA TGACGTCCCT TGCCATTTTC CTTTTCCTGA
1701  TGCGGGATGA GGAGGGGGAG GACGTCCCTC TGCGGGTACG AACTGTGCAT
1751  TGTGTCTGTT AACATCAACT GGGCTGGCTG GCAGGGGTG TTGGCACAGA
1801  CCTTTAATCC CAGCACTAGG GAGGCTAAAG CAGGAGCATC TCTACGATTT
1851  CGAGACCAGC CTGATTCACA TAGCGATACC AACCATCTGA AGAAAGGGGT
1901  GGGGGGTGTT TACTGCCCAG GCTGGCCTTA ATCCTTCTTC GGGCTTCGGA
1951  GCTCAGGAAA ACCCAGTACC AGTGGGTTTT TCTTGCTTCG GCAGTGTCT
2001  CTCTGCAATG TTGCCTCCCT GGGACAGGTG GTGGTGGTGG TGGTGGTGGT
2051  GGTGGTGGTG GTGGTGGTGG TGGTGGTGGT GGTGGTGTGT GAATATTTAC
2101  TGTTTTACAC AAAACACTGC ACCGTCCGTT TTTCCAACAG TTCATGAGGA
2151  TTCCAACACC AAGCCATTCT ATAAATAAGA AGCCGAGTCT CAGAGAATTT
2201  GAGTGTGTAG AGAAAGGAGG TCCGCAGGCC CAGTTCTGTG CATCATAGGG
2251  TGTTCCGGGG TGTCTGGCTG TATCTCAAGA TTCTCTCAGA AAATCACCCG
2301  CACCGGACCG GATCCCTCAG GGAGGGGCTG CACTTTGGTT CTTCTCTTCT
2351  GCACCCGGAT GAAGCAGGAA CCCCGGTTGC GTGTTGCACT GAACGCTAAA
2401  GGGTTAAGGC CTGGGGGGCC GCCCCTTTTC CGCCCAGCCG GCGGGAGTAT
2451  GAATACCCTC GCTCCAGCTC CCTGCTGGAG TTCTCCGCTT CCGCTGGGTC
2501  ACTGTCGCCG CTACTTCTTT TCAACCCCTA AAAGCTCCAC GGGCCACTCC
2551  CTTCTCTAGT GCTCCACGTC CGCTTGCCCT CGGGGGCCAG ACCAGCGACA
2601  TGGAGGGTTG CGTCGGGGAA GAATCTTTTC AGATGTGGGA GCTCAATCGA
2651  CGCCTGGAGG CCTACCTGAC CCGGGTCAAG ACGCTAGAAG AGCAAAACCA
2701  GCTGCTCAGC GCCGAGCTTG GGGGACTCCG GCGCAGTCC GGAGACACCT
2751  CCTGGAGAGC CCGAGCCGAT GACGAGCTGG CATCCCTGCG GATCCTCGTC
2801  GATCAGCGCT GGCGGGAGAA GCTCGAGGCT GAGGTGCAGC GCGACAACCT
2851  TGCGGAAGAG CTGGAGAGCG TGGCGGGCCG GTGCCAGCAG GTGCGGCTTG
```

Figure 1C

```
2901  CTCGGGAGCG GACCGTCCAG GAGGCCGCCT GCAGCCGGCG CGCACTCGAG
2951  GCGGAGAAGA ATGCGCGGGG CTGGCTGAGC ACCCAGGCGG CCGAGCTGGA
3001  GCGGGAGTTA GAGGCTCTGC GAGCCGCGCA CGAGGAGGAG CGCGCACACC
3051  TGAACGCCCA GGCCGCCTGT GCGCCTCGCC GGCCCCCGC ACCGCCCAC
3101  GGATCCCCGG TCCGGCCCC CGAAGTCGAG GATCTGGCCA GGCGACTAGG
3151  CGAAGTGTGG CGCGGGGCGG TGCGTGACTA CCAGGAGCGC GTGGCTCACA
3201  TGGAAAGCTC GCTGGGTCAG GCACGCGAGC GGCTGAGCCA AGCCGTGCGG
3251  GGCGCTCGGG AGTGTCGCTT AGAGGTGCAA CAGCTGCAGG CTGATCGCGA
3301  CAGCCTCCAG GAGCGCAGAG AAGCGCTGGA ACAGAGATTG GAAGGCCGCT
3351  GGCAGGACCG GCTGCAGGCC ACTGATAAGT TCCAGGTGAG GAGGGTCACC
3401  AACTTCCTCC CCGACTACCC GCCCCACAC AGACCCGTAA GACCAAGCCC
3451  TAGGAAGTAC TTAGGATGGC AAGAGACCTT CAGGAAGGGG CTGGAGGAAA
3501  GGGCGACTGT ATTCATGAGT CCTGCCCAGA GCAAGCACAG GCCCTAAACT
3551  TTCCTGTCCA AGCAGGATGG GCGGATGGAA TTCTGAGACC TCCTTAGCAG
3601  AGCCCGCTTA AAGGACGACA GGCCAATTCC CACTGTAGCA GCTCCTCACT
3651  CTTTGAAGGG CAATTTCACT CTAGGATGAT TCCCTGCGCC CTTCCCTTTG
3701  CTGTTGTCAA TCAGAAGGTG CCCAGCACAT GCTCCCTCAG CACCAGAAGG
3751  TCCCTAGCAA CCATAGTGAA GGAAGGCGGG GTGAGCCACC GCCGACCACC
3801  AGCCCCTCTC TGTGTCAAGG CTTCTCAGCT CCCTGAAGCA CATTCCAAAG
3851  GCCTGGGGCA CCCTCCCCCT TATACTGCAC AGATGTAACC AACAGCTGAG
3901  AAAACAGCTC TTGCCTGGCC CAGACAGAAG CCCCGACACG GCCATCTGCC
3951  CACTCTTCTT GGGGGAGAAA GATTCCAGAA CACGTGGGAA GTGGAGGAAC
4001  CCAGCCTGCT ATGAGGAGCT GGGGACAGTG ATGGCCAACG GATTTCCTTC
4051  CACGTCCTCC CAAGCCGACT CTTGATAAAT TGCTTTTCCC TTCTGTTTCC
4101  ATTTTACCTC CTCTTCTGCT GTGTAACCCA TCCCCGTGGG AGCTAGATTC
4151  TCAATAGCAT GTGTTACCAT TTAATGAGCA TCCTCAAGAG AAGCCTGGTC
4201  TAGGAGAGGC ATGGAGTGTT CCCTGAGCTT GTCTGTGGGT TCCAGTGCAG
4251  GGAGGACATA GAACAGGAGT CCTACAGAGA AGTGAGCAGT AAGGAGCCTC
4301  AGGGCCAGAG CGGAGGCTCC TTCCACTCAC TCTTCCCGCT TGCCTTGCAG
4351  CTGGCTGTGG AAGCCCTGGA GCAGGAGAAG CAAGGTCTAC AGAGTCAGAT
```

Figure 1D

```
4401  CGCTCAGATC CTGGAAGGTG GGCAGCAACT GGCACACCTC AAGATGTCCC
4451  TTAGTCTGGA GGTGGCTACA TACAGGTACA CAGTGCTGAC TGTCCTCGGC
4501  TTCTTCTGCG GCCCAGAAAC TTGGCTTTGT ACTTTCTGTG ACTGTCAGCT
4551  ATCGCTTTGT AAAACTGTCC TATTTATGTG TATTTGTGTA TGTACCACAT
4601  GTGTACAGGT GTCCTAAGAG CCCAGAGGAA GGCAATGGGT TGTGTGCAGC
4651  TCCACACTGG TGCTGTGAAC CAAACCCCTG TTCTCAGCAA AAAGCAGCAA
4701  GCATTCTTAA CCACTGAGCC GTCTGTCCAG CCCTCGGAGT CACTTAAAAC
4751  GTTTTATAAC ATTTACTTAT GTAATGTATT TGTCTGGGAT GGAGGCTTAT
4801  GAGTCCCAGA GGTGGAACAG GTCTGGCTTG GCAGCTTGGC CCACCCAGGC
4851  CCAGGACCAG AAGAGAGCGG TGATGCTTAA AAAGACAGCT CAGTCTTCAG
4901  GGAGGAGACC AGACAGATGA GTTCTTTGGA AGGCAGGCAA TCTCCAGTGT
4951  CTATGCCAAC ATCCTGGGGA CACCTGGGCA GTCTCAGAAG AGAGGCCTTG
5001  CAGGTTTGCC TGATCATGCT AACCTGCCAC CTCGCCTGGG CCTCAGGTGT
5051  TTTGGGTAAG AGCTGGCCTC CTAGCTTTTT TGCTTCCTTT CAAGCCCTCA
5101  TGTCACTGGT CCTGCCCCAG TTCTCTGCCC TTTTCTTGGC TGCCTCAGGA
5151  CGGCTGAGTG GAACGGCTCT GGTGGTATGT TCACAGCCTC TGTCTGTGTC
5201  TCTTGTGGGA AAAGGCCCCA GTTGGAGTCC CACGGTTGAG GGCTGAGGAT
5251  ATCACTCCAG GTATGGGCTA GGACAGGATG CCCCCCTTTT CCAGAATCCA
5301  GCGGTAAAGA GGAAAGACAG AGACAGGTCT AGGAGAGGAG CTGGAGGGCC
5351  CAGAGAAGGA CAGCCAGTGA GTGTCTAGGA AAGACTGAAT GCATAAGGCA
5401  GGATGCCGCA TGAGGACAGA GGAAAGGCTA CTTTGAGAAC CAGATGTGCT
5451  CAGAGGCCAT GAATGGAAAC AGACTAGTTC CGAATCCCAT GTGAACTGAT
5501  TTCCCTCATC TCCTTCAATC AGCTCCATAG GCCACTGAGG CAGGGCCATG
5551  AACGTTAAGA CCTCTGCCCT GAAGAGTTTG TGATCCTGAG ATGAGGGCTT
5601  TAGCCCCAGT CAGTCCTCTG AGGGGAAGGG TCCAGGCAGC TCTGAGGAAT
5651  GTAACCACTG GCGTTTGAGG TCTGAAAAGG ATTTGGAGAA GGGGAGCTGA
5701  ATTCATTTGC TTTTGTCTGT TACCAGCTCT GGGGGCAGAG AGAGAGCCAT
5751  CCCCTGGGAA CAGCCTGAGA ATTCCCACTT CCCCTGAGGA GCCCTCCCTT
5801  CTTAGGCCCT CCAGATGGTA GTGTGGACAA AAGGCAATAA TTAGCATGAG
5851  AATCGGCCTC CCTCCCAGAG GATGAGGTCA TCGGCCTTGG CCTTGGGTGG
```

Figure 1E

```
5901  GGAGGCGGAG ACTGATCTGA GGAGTCTGAT ATAAGTGTTA GCAATTCATT
5951  TGGCCCTGCC TCCGACTGTG GGAATCTGCA TGTGGGGTCT CCCTGTGTCT
6001  CAAATATGGG TTGGCTAAGT ATATATCTGT GTGGCTTTTA TATGACAATG
6051  GTCACAATAG AGATTGATCC TGCAGTGGCA GGACATGCTA CCTCAGCTGG
6101  AGCTGACCCT ATCTCCCCAC TCCCCACCAG GACTCTGCTG GAGGCTGAGA
6151  ACTCTCGGTT GCAGACACCT GGACGAGGTT CCCAGGCTTC TCTTGGCTTT
6201  CTGGGTAAGA GGCGGAGCCT AACTGCTCTC CTTGGAAGAT CTTCCCTAAG
6251  CAGCATCAGT CTAAGCCTTC ATTCCCTGGT CCCAACCCTA CTGATGTTCT
6301  CAGTCTAGCC AGTGGGGGTC AGACAAAATG ACCAATGTGA GAACTGCTCT
6351  GGGCTGAGGT CAGGACATAC TTACAGTGTT TCTTACTCTG CTTTTCCAGA
6401  CCCCAAGCTG AAGCCGAATT TCCTTGGGAT ACCAGAGGAC CAGTACCTGG
6451  GATCTGTGCT CCCTGCCCTC AGCCCCACAT CCTTCCCTTC CCCCTTGCCT
6501  AATACCCTTG AGACTCCTGT GACAGCCTTC CTGAAGACTC AGGAGTTCCT
6551  TCAGGCCAGA ACCCCCACCT TGGCCAGCAC TCCCATCCCA CCTATATCTG
6601  AGGCTCCCTG TCCTCCAAAT GCAGAGGTGA GAGCCCAGGA GGTCCCTCTT
6651  TCTCTGCTCC AGACACAGGC TCCAGAGCCC CTTTGGCTGA AGGCCACAGT
6701  GCCTAGTTCT TCTGCTATCC TCCCAGAACT AGAGGAACCT GGGGGCAAGC
6751  AGCAGGGTCA CTTCCCTGAT GATCTGACCT CCTTAGCCAC AAACCTCAAC
6801  CCTCACCACC CTACTTTAGA GGCTAAAGAT GGAGAATCCA GTGAGTCTAG
6851  AGTTTCTAGC ATATTCCAGG AAGATGAGGG GCAAATCTGG GAACTGGTAG
6901  AGAAAGAAGC AGATATAGAG GTAAAGTAG AAAACAGCTC AGCCCAGAAA
6951  ACACAAGAAA GTGGTCTGGA CACAGAAGAA ACCCAGGATT CCCAGGGACC
7001  TTTGCAGAAG GAAACACTGA AGGCTCTAGG AGAGGAGCCA CTGATGTCTC
7051  TGAAAATCCA GAACTATGAG ACAGCAGGGA AAGAGAATTG CAATTCTTCT
7101  ACAGAAGGCC ACCTGGGAAC ACTAGAAGGC CCAGAAAAAG AAAAGCAAAT
7151  ACCACTAAAG TCTTTAGAAG AAAAGAATGT AGAGTCAGAG AAAACTCTAG
7201  AAAATGGGGT TCCTGTACTA TCTGAGCTTT TAGGAAAAGA AGACACAAGA
7251  ACAGAGGATC AAGAATTAAT GTCTCCTAAA GGTACACTAA AGAGATTTTC
7301  ATCTCTAGGA AAGGAAAGTC AAGAAGTAGT GAGGCCTTCA AAAGAGGGGA
7351  ACCTAGAATC ATGGACAGCT TTTAAAGAGG AGAGCCAACA CCCACTGGGA
```

Figure 1F

```
7401  TTTCCAGGAG CTGAGGACCA GATGCTTGAG AGACTGGTAG AGAAAGAGGA
7451  TCAGAGCTTC CCAAGGTCTC CAGAGGAAGA GGACCAGGAG GCATGTAGAC
7501  CTCTGCAGAA AGAGAATCAG GAACCACTAG GGTATGAAGA AGCAGAGGGC
7551  CAGATACTTG AGAGACTGAT AGAAAAAGAG AGTCAGGAGT CCCTGAGGTC
7601  TCCAGAAGAA GAGGACCAGG AGGCAGGTAG ATCTCTGCAG AAAGAGAATC
7651  AGGAGCCACT AGGGTATGAA GAAGCAGAGG ACCAGATGCT TGAGAGACTG
7701  ATAGAAAAAG AGAGTCAGGA GTCCCTGAAG TCTCCAGAAG AAAACCAGAG
7751  GATTGGGAAG CCTCTAGAAA GAGAGAATCA GAAATCTCTG AGGTATCTTG
7801  AAGAAAACCA GGAGACTTTT GTACCACTAG AAAGCAGGAA CCAGAGGCCA
7851  CTGAGATCTC TAGAAGTAGA AGAGGAGGAG CAGAGAATTG TGAAACCTCT
7901  AGAAAAAGTG AGTCAGGATT CCCTCGGATC TCTAGCAGAA GAGAATGTGC
7951  AGCCACTGAG GTATCTGGAA GAAGATGACT GCATAAATAA GAGCCTTCTA
8001  GAAGACAAGA CTCACAAGTC CTTGGGGTCT CTTGAAGATA GAAATGGGGA
8051  TAGCATTATT ATACCACAAG AAAGTGAGAC CCAGGTTTCA TTGAGGCCTC
8101  CAGAAGAGGA GGACCAGAGG ATTGTGAACC ATCTAGAAAA AGAAAGTCAG
8151  GAGTTCTCGA GGTCTTCAGA AGAAGAAGAG CAGGTGATGG AGAGATCTCT
8201  AGAAGGAGAG AACCATGAAT CACTGAGTTC TGTAGAAAAA GAGGACCAGA
8251  TGGTTGAGAG CCAACTAGAG AAAGAGAGTC AGGACTCAGG GAAGTCTCTT
8301  GAAGATGAGA GCCAGGAGAC CTTTGGACCT CTGGAAAAAG AGAATGCAGA
8351  GTCCCTGAGA TCTCTAGCAG GACAGGACCA AGAGGAACAG AAGCTTGAAC
8401  AAGAGACCCA ACAAACACTG AGGGCTGTAG GAATGAGCA GATGGCAGTG
8451  AGCCCACCAG AAAAGGTGGA TCCAGAGTTA CCGAAGCCTC TTGGAAATGA
8501  CCAGGAAATA GCTAGATCTC TTGGAAAAGA GAATCAAGAG TCACTAGTGT
8551  CACTGAAAGA AAAAGGTATA GAGACAGTGA AGTCTTTAGA AACAGAGATC
8601  ATAGAACCAC TGGAGACTGC AGAAGAGGAC CTGGAAAGAA GGAAGTCTAT
8651  AGATACTCAG GAGCCATTGT GGTCTACTGA AGTGGCTAGA GAGACAGTAG
8701  AACCTCCAGA AGATGAGCCC CCAGGATCGC TAGGGTCTGT GGATGAGAAC
8751  CGAGAGACAC TGACATCCCT TGAAAAGGAG AGTCAAGAAC TGAGCTCTCT
8801  GGGCAAGTGG AACGTAGAGA CCAGGGTAGA GGACAGTCAG CAGTGCCTGC
8851  AAGTAGAAGA GGGTCTGCAG GAGGAACAGC ACCAAGAGTC TCTGAGAGAG
```

Figure 1G

```
8901  GTGAAGCAGG AGCTGCCTAG CTCTGGAAAT CAACAGCGGT GGGAGGATGT
8951  GGTGGAGGGC AAAGCAGTGG GTCAGGAAGC ACCTCTGGCA ACCACAGGAG
9001  TGGGAACTGA GGATAAGGCA GAGTTGCATC TGAGGGGGCA AGGTGGAGAG
9051  GAAGAAGCTG CAGCAGAGGG AGAGCTGTTG CAGGATATTG TGGGGGAGGC
9101  CTGGAGTCTG GGGAGCTCTG AGCCCAAGGA GCAGAGGGTC CCTGCTGAGG
9151  CCCTCGACAA CCTGGAAGGA GGGGCCTTAG AGGTCCCAGT TGCTCAGTCA
9201  ATGCCAGAGG TGACAGAGCG AGATGAGGAT AGAGCCCAAG CAGGTGAACA
9251  AGACTCCATA GAGGTGACCC TTGGGTTAGA GGCTGCCAGA ACTGGACTGG
9301  AACTCGAGCA GGAAGTGGTA GGGCTAGAGG ACCCAAGGCA TTTTGCCAGG
9351  GAGGAGGCCA TTCCCCCATC CCTGGGGAG GAAAGTGTGA AGGCAAAGAT
9401  AGCTCAGGGC TTGGAAGGGC CTGGAAAGGA ACCAAAAGAG GCAGGTGCTC
9451  TGGACTCGGG GATCCTTGAA TTGCCCAAGA CTAGCAGCGA GGCTCTGGAA
9501  TGCCAGGGCC ATGAAGAGTC TGAGTCCATG GAGGGCTGGG AAGAAGAGGA
9551  GGCCTCACTG GAGACTTCAG ATCATGAGGG CAGTGATGCC CCTCAGCCCA
9601  GGCCCCCAGA AACAGAAGAA GATGAGGGTG CACAGGCAGC ACTGACAGCC
9651  CCTGGTCCCA AGCTCTTGGA ACCCTGTTCA CCCATCCCAA TCCTGACAGA
9701  TGCCCATGAG CTGCAGCCCC AGGCTGAGGG GATCCAGGAG GCTGGCTGGC
9751  AGCCAGAAGC TGGGTCTGAA GCACTAGAAA GGGTAGAAAA TGAGCCAGAG
9801  TTTGGTCTTG GGGAGATCCC GGAGGGCCTC CAGGATTGGG AAGAGGGCAG
9851  AGAAGAAAGC GAGGCAGATG ATCTAGGGGA AACTCTCCCT GACTCTACTC
9901  CCCTGGGCCT CTACCTGAGG TCCCTGCTT CTCCAAAGTG GGATCTGGCT
9951  GGAGAACAGA GGCTTTCCCC TCAAGGGGAT GCCGGGAAGG AAGACTGGGG
10001 TCCTGCTGTC CCCGCTGCCC AGGGCCTCAG TGGTCCACCG GAAGAGGAGG
10051 AGGAGCAAGG CCATGGCTCT GACCTATCAT CTGAGGAGTT TGAGGACCTA
10101 GGGACTGAGG CCTCTCTTCT TCCAGGGGTT CCCAAGGAGG TGGCAGATCA
10151 CGTGGGCCAA GTGCCCCCGG TACTGCAGCC TGCATGCTGG GATCAGGGTG
10201 GGGAATCTGA TGGGTTTGCT GATGAGGAAG AAAGTGGGGA GGAGGGAGAG
10251 GAAGAAGATG CTGATGAGGA AGGAGCAGAG TCAGGAGCTC AGTGGTGGGG
10301 GTCAGGGGCC TCTGGTGGAG GCTGCAAGGT CCAGGATATT GCCCAAAGAG
10351 GAGACCCGGT ACAGGAGTCT GTGGGTGTCA GTGGTCTCTG GGATGATGGC
```

Figure 1H

```
10401  TTGAGAGGTG CTGCAGCTAA TGTTCCTGCC CTAGAGATGG TATCTCAGGA
10451  CAGTGCTGAG CCTTCTGGGT CAGAGGAGTC TGAGTCTGCT TCCTTGGAGG
10501  GGGAGGAAGG TCAAGTGACT GACCATTTAG ATGCTCCCCA GGAGGTGACC
10551  AGCATGGTCC CGGGGGTAGG AGATGCCTTT GACATTGGTG GCCAGAGCCC
10601  CAACTTGGAC TCAGAACAAG TGAATGGGAA AATGGAGAAT GGACTAGAAC
10651  AGGCTGAGGG GCAGGTGGTC CTGGATGGGG ACGAGGATCA AGAACTCCTA
10701  TTACAGGGAC AGGAGGTGGG TGCTCTAAAG GTTCCTTTGG TAGCATCTCC
10751  TGTGCATCTA GGCCCAAGCC AGCCCCTGAA GTTCACTCTG AGTGGGGTAG
10801  ATGGGGATTC CTGGTCCTCA GGGGAAGACT AGAAACTGCC CCTCTGGCTC
10851  TGAGGATGTA CTGGTGGGA TGTCCCTCCC TGCTCTGGGT GACCACTCTT
10901  AGCTTTGATA ACTTGACCCA TGGTATTTGT CCTGGAGAGT TGTGGCTGGG
10951  CTGAGCAAGG GAGGTGAGAT CCTCCTGAAG GCTCAGGAGT TCCAGGCCTA
11001  TAGTTCTACC CCCTCTTTCT TCTGTGGCTC ACCTGCTGGA AGAGGCCTGG
11051  GCCCAGAGCT TTCCCACAAG GCTGTTCTGG CCACAGCTTG CTAGCCTTGC
11101  CTACCACCTG CACAAGGTCT GGTCTGGTGT ATGACCAGGG GAGCTGAGGG
11151  CAGCATTTAT CTGACCCTTC ATCTCAGCCT GCTGAGAGCT TGTTCCTCTC
11201  TTCCTCCCTG AATAAAGCCG TATCCCTACC TACAAAAAAA AAAAAAA
```

Figure 2

```
MEGCVGEESFQMWELNRRLEAYLTRVKTLEEQNQLLSAELGGLRAQSGDTSWRARADDELASLRI
LVDQRWREKLEAEVQRDNLAEELESVAGRCQQVRLARERTVQEAACSRRALEAEKNARGWLSTQA
AELERELEALRAAHEEERAHLNAQAACAPRRPPAPPHRIPGPAPEVEDLARRLGEVWRGAVRDYQ
ERVAHMESSLGQARERLSQAVRGARECRLEVQQLQADRDSLQERREALEQRLEGRWQDRLQATDK
FQLAVEALEQEKQGLQSQIAQILEGGQQLAHLKMSLSLEVATYRTLLEAENSRLQTPGRGSQASL
GFLDPKLKPNFLGIPEDQYLGSVLPALSPTSFPSPLPNTLETPVTAFLKTQEFLQARTPTLASTP
IPPISEAPCPPNAEVRAQEVPLSLLQTQAPEPLWLKATVPSSSAILPELEEPGGKQQGHFPDDLT
SLATNLNPHHPTLEAKDGESSESRVSSIFQEDEGQIWELVEKEADIEVKVENSSAQKTQESGLDT
EETQDSQGPLQKETLKALGEEPLMSLKIQNYETAGKENCNSSTEGHLGTLEGPEKEKQIPLKSLE
EKNVESEKTLENGVPVLSELLGKEDTRTEDQELMSPKGTLKRFSSLGKESQEVVRPSKEGNLESW
TAFKEESQHPLGFPGAEDQMLERLVEKEDQSFPRSPEEEDQEACRPLQKENQEPLGYEEAEGQIL
ERLIEKESQESLRSPEEEDQEAGRSLQKENQEPLGYEEAEDQMLERLIEKESQESLKSPEENQRI
GKPLERENQKSLRYLEENQETFVPLESRNQRPLRSLEVEEEEQRIVKPLEKVSQDSLGSLAEENV
QPLRYLEEDDCINKSLLEDKTHKSLGSLEDRNGDSIIIPQESETQVSLRPPEEEDQRIVNHLEKE
SQEFSRSSEEEEQVMERSLEGENHESLSSVEKEDQMVESQLEKESQDSGKSLEDESQETFGPLEK
ENAESLRSLAGQDQEEQKLEQETQQTLRAVGNEQMAVSPPEKVDPELPKPLGNDQEIARSLGKEN
QESLVSLKEKGIETVKSLETEIIEPLETAEEDLERRKSIDTQEPLWSTEVARETVEPPEDEPPGS
LGSVDENRETLTSLEKESQELSSLGKWNVETRVEDSQQCLQVEEGLQEEQHQESLREVKQELPSS
GNQQRWEDVVEGKAVGQEAPLATTGVGTEDKAELHLRGQGGEEEAAAEGELLQDIVGEAWSLGSS
EPKEQRVPAEALDNLEGGALEVPVAQSMPEVTERDEDRAQAGEQDSIEVTLGLEAARTGLELEQE
VVGLEDPRHFAREEAIPPSLGEESVKAKIAQGLEGPGKEPKEAGALDSGILELPKTSSEALECQG
HEESESMEGWEEEEASLETSDHEGSDAPQPRPPETEEDEGAQAALTAPGPKLLEPCSPIPILTDA
HELQPQAEGIQEAGWQPEAGSEALERVENEPEFGLGEIPEGLQDWEEGREESEADDLGETLPDST
PLGLYLRSPASPKWDLAGEQRLSPQGDAGKEDWGPAVPAAQGLSGPPEEEEQGHGSDLSSEEFE
DLGTEASLLPGVPKEVADHVGQVPPVLQPACWDQGGESDGFADEEESGEEGEEEDADEEGAESGA
QWWGSGASGGGCKVQDIAQRGDPVQESVGVSGLWDDGLRGAAANVPALEMVSQDSAEPSGSEESE
SASLEGEEGQVTDHLDAPQEVTSMVPGVGDAFDIGGQSPNLDSEQVNGKMENGLEQAEGQVVLDG
DEDQELLLQGQEVGALKVPLVASPVHLGPSQPLKFTLSGVDGDSWSSGED
```

Figure 3A

```
   1  ATGGAGGGCT GCATGGGGGA GGAGTCGTTT CAGATGTGGG AGCTCAATCG
  51  GCGCCTGGAG GCCTACCTGG GCCGGGTCAA GGCGCTGGAG GAGCAGAATG
 101  AGCTGCTCAG CGCCGGACTC GGGGGGCTCC GGCGACAATC CGCGGACACC
 151  TCCTGGCGGG CGCATGCCGA CGACGAGCTG GCGGCCCTGC GTGCGCTCGT
 201  TGACCAACGC TGGCGGGAGA AGCACGCGGC CGAGGTGGCG CGCGACAACC
 251  TGGCTGAAGA GCTGGAGGGC GTGGCAGGCC GATGCGAGCA GCTGCGGCTG
 301  GCCCGGGAGC GGACGACGGA GGAGGTAGCC CGCAACCGGC GCGCCGTCGA
 351  GGCAGAGAAA TGCGCCCGGG CCTGGCTGAG TAGCCAGGGG GCAGAGCTGG
 401  AGCGcGAGcT AGAGGCTcTA CGCGTgGCGC ACGAGGAGGA GCGCGTCGGT
 451  CTGAACGCGC AGgCtgCCTG TGCCCCCCGc cTGCCCgcGc cgcCCCgGcc
 501  tcccgcgCCG GCCCCGGAGG tAGAGGAGcT GGcAAGGCGA CTGGGCGAGG
 551  CGTGGCGCGG GGCAGTGCGC GGCTACCAGG AGCGCGTGGC ACACATGGAG
 601  ACGTCGCTGG ACCAGAcCCG CGAGCGCCTG GCCCGGGCGG TGCAGGGTGC
 651  CCGCGAGGTC CGCCTGGAGC TACAGCAGCT CCAGGCTGAG CGCGGAGGCC
 701  TCCTGGAGCG CAGGGCAGCG TTGGAACAGA GGTTGGAGGG CCGCTGgcag
 751  GaGcGGcTGC GGGCtACTGA AAAGTTCCAG CTGGCTGTGG AGGCCCTGGA
 801  GCAGGAGAAA CAGGGCCTAC AGAGCCAGAT CGCTCAGGTC CTGGAAGGTC
 851  GGCAGCAGCT GGCGCACCTC AAGATGTCCC TCAGCCTGGA GGTGGCCACG
 901  TACAGGACCC TCCTGGAGGC TGAGAACTCC CGGCTGCAAA CACCTGGCGG
 951  TGGCTCCAAG ACTTCCCTCA GCTTTCAGGA CCCCAAGCTG GAGCTGCAAT
1001  TCCCTAGGAC CCCAGAGGGC CGGCGTCTTG GATCTTTGCT CCCAGTCCTG
1051  AGCCCAACTT CCCTCCCCTC ACCCTTGCCT GCTACCCTTG AGACACCTGT
1101  GCCAGCCTTT CTTAAGAACC AAGAATTCCT CCAGGCCCGT ACCCCTACCT
1151  TGGCCAGCAC CCCCATCCCC CCCACACCTC AGGCACCCTC TCCTGCTGTA
1201  GATGCAGAGA TCAGAGCCCA GGATGCTCCT CTCTCTCTGC TCCAGACACA
1251  GGGTGGGAGG AAACAGGCTC CAGAGCCCCT GCGGGCTGAA GCCAGGGTGG
1301  CCATTCCTGC CAGCGTCCTG CCTGGACCAG AGGAGCCTGG GGGCCAGCGG
1351  CAAGAGGCCA GTACAGGCCA GTCCCCAGAG GACCATGCCT CCTTGGCACC
1401  ACCCCTCAGC CCTGACCACT CCAGTTTAGA GGCTAAGGAT GGAGAATCCG
1451  GTGGGTCTAG AGTGTTCAGC ATATGCCGAG GGAAGGTGA AGGGCAAATC
```

Figure 3B

```
1501  TGGGGGTTGG TAGAGAAAGA AACAGCCATA GAGGGCAAAG TGGTAAGCAG
1551  CTTGCAGCAG GAAATATGGG AAGAAGAGGA TCTAAACAGG AAGGAAATCC
1601  AGGACTCCCA GGTTCCTTTG GAAAAAGAAA CCCTGAAGTC TCTGGGAGAG
1651  GAGATTCAAG AGTCACTGAA GACTCTGGAA AACCAGAGCC ATGAGACACT
1701  AGAAAGGGAG AATCAAGAAT GTCCGAGGTC TTTAGAAGAA GACTTAGAAA
1751  CACTAAAAAG TCTAGAAAAG GAAAATAAAA GAGCTATTAA AGGATGTGGA
1801  GGTAGTGAGA CCTCTAGAAA AAGAGGCTGT AGGCAACTTA AGCCTACAGG
1851  AAAAGAGGAC ACACAGACAT TGCAATCCCT GCAAAAGGAG AATCAAGAAC
1901  TAATGAAATC TCTTGAAGGT AATCTAGAGA CATTTTTATT TCCAGGAACG
1951  GAAAATCAAG AATTAGTAAG TTCTCTGCAA GAGAACTTAG AGTCATTGAC
2001  AGCTCTGGAA AAGGAGAATC AAGAGCCACT GAGATCTCCA GAAGTAGGGG
2051  ATGAGGAGGC ACTGAGACCT CTGACAAAGG AGAATCAGGA ACCCCTGAGG
2101  TCTCTTGAAG ATGAGAACAA AGAGGCCTTT AGATCTCTAG AAAAAGAGAA
2151  CCAGGAGCCA CTGAAGACTC TAGAAGAAGA GGACCAGAGT ATTGTGAGAC
2201  CTCTAGAAAC AGAGAATCAC AAATCACTGA GGTCTTTAGA AGAACAGGAC
2251  CAAGAGACAT TGAGAACTCT TGAAAAGAG ACTCAACAGC GACGGAGGTC
2301  TCTAGGGGAA CAGGATCAGA TGACATTAAG ACCCCCAGAA AAAGTGGATC
2351  TAGAACCACT GAAGTCTCTT GACCAGGAGA TAGCTAGACC TCTTGAAAAT
2401  GAGAATCAAG AGTTCTTAAA GTCACTCAAA GAAGAGAGCG TAGAGGCAGT
2451  AAAATCTTTA GAAACAGAGA TCCTAGAATC ACTGAAGTCT GCGGGACAAG
2501  AGAACCTGGA AACACTGAAA TCTCCAGAAA CTCAAGCACC ACTGTGGACT
2551  CCAGAAGAAA TAAATAAATC AGGGGGCAAT GAATCCTCTA GAAAAGGAAA
2601  TTCAAGAACC ACTGGAGTCT GTGGAAGTGA ACCAAGAGAC ATTCAGACTC
2651  CTGGAAGAGG AGAATCAGGA ATCATTGAGA TCTCTGGGAG CATGGAACCT
2701  GGAGAATTTG AGATCTCCAG AGGAGTAGAC AAGGAAAGTC AAAGGAATCT
2751  GGAAGAGGAA GAGAACCTGG GAAAGGGAGA GTACCAAGAG TCACTGAGGT
2801  CTCTGGAGGA GGAGGGACAG GAGCTGCCGC AGTCTGCAGA TGTGCAGAGG
2851  TGGAAGATA CGGTGGAGAA GGACCAAGAA CTGGCTCAGG AAAGCCCTCC
2901  TGGGATGGCT GGAGTGGAAA ATAaGgatga Ggcagagctg AatctAaGGg
2951  agcaGgatGG CTTCACTGGG AAGGAGGAGG TGGTAGAGCA GGGAGAGCTG
```

Figure 3C

```
3001  AATGCCACAG AGGAGGTCTG GTTCCCAGGC GAGGGGCACC CAGAGAACCC
3051  TGAGCCCAAA GAGCAGAGAG GCCTGGTTGA GGGAGCCAGT gTGAAGGGAg
3101  GGgctgagGg cctCcaggac CCtgaAgGGC AATCACAACA GGTGGGGAcC
3151  CCAGGcCTCC AGGCTCCCCA GGGgctgCca gaGgcgatag agCCcctGgt
3201  GgAagatgaT GTGGCCcCAG GGGGTGACca AGCCTCCCCA GAGGTCATGT
3251  TGGGGTCAGA GCCTGCCATG GGTGAGTCTG CTGCGGGagC TGAGCCAGgc
3301  ctGGGgcaGG GGgtGGgaGG gCtGGGGgaC CcaggCcATC TgACCAGGGA
3351  AGAGGTGATG GAACCACCCC TGGAAGAGGA GAGTTTGGAG GCAAAGAGGG
3401  TTCAgGGCTT GGAAGGGCCT AGAAAGGACC TAGAGGAGGC AGGTGGTCTG
3451  GGGACAGAGT TCTCCGAGCT GCCTGGGAAG AGCAGAGACC CTTGGgAGCC
3501  TCCCAGGGAG GGTAGGGAGG AGTCAgAGGC TGAGGCCCCC AGGGGAGCAG
3551  AGGAGGCGTT CCCTGCTGAG ACCCTGGGCC ACACTGGAAG TGATGCCCCT
3601  TCACCTTGGC CTCTGGGGTC AGAGGAAGCT GAGGAGGATG TACCACCAGT
3651  GCTGGTCTCC CCCAGCCCAA CGTACACCCC GATCCTGGAA GATGCCCCTG
3701  GGCTrCAGCC TCAGGCTGAA GGGAGTCAGG AGGCTAGCTG GGGGGTGCAG
3751  GGGAGGGCTG AAGCTGGGAA AGTAGAGAGC GAGCAGGAGG AGTTGGGTTC
3801  TGGGGAGATC CCCGAGGGCC TCCAGGAGGA AGGGGAGGAG AGCAGAGAAG
3851  AGAGCGAGGA GGATGAGCTC GGGGAGACCC TTCCAGACTC CACTCCCCTG
3901  GGCTTCTACC TCAGGTCCCC CACCTCCCCC AGGTGGACCC CACTGGAGAG
3951  CAGAGGCCAC CCCCTCAAGG AGACTGGAAA GGAGGGCTGG GATCCTGCTG
4001  TCCTGGCTTC CGAGGGCCTT GAGGArCCCT CAGAAAGGA GGAGGGGAG
4051  GAGGGAGAAG AGGAGTGTGG CCGTGACTCT GACCTGTCAG AAGAATTTGA
4101  GGACCTGGGG ACTGAGGCAC CTTTTCTTCC TGGGGTCCCT GGGGAGGTGG
4151  CAGAACCTCT GGGCCAGgtg cCcCagCTGC TACTGGATCC TGCAGCCTGG
4201  GATCGAGATG GGGAGTCTGA TGGGTTTGCA GATGAGGAAg AAAGTGGGGA
4251  GGAGGGAGAG GAGGATCAGG AGGAGGGGAG GGAGCCAGGG GCTGGGCGGT
4301  GGGGGCCAGG GTCTTCTGTT GGCAGCCTCC AGGCCCTGAG TAGCTCCCAG
4351  AGAGGGGAAT TCCTGGAGTC TGATTCTGTA AGTGTCAGCG TCCCCTGGGA
4401  TGACAGCTTG AGGGGTGCAG TGGCTGGTGC CCCCAAGACT GCCCTGGAAA
4451  CGGAGTCCCA GGACAGTGCT GAGCCTTCTG GCTCAGAGGA AGAGTCTGAC
```

Figure 3D

```
4501  CCTGTTTCCT TGGAGAGGGA GGACAAAGTC CCTGGCCCTC TAGAGATCCC
4551  CAGTGGGATG GAGGATGCAG GCCCAGGGGC AGACATCATT GGTGTTAATG
4601  GCCAGGGTCC CAACTTGGAG GGGAAGTCAC AGCATGTAAA TGGGGGAGTA
4651  ATGAACGGGC TGGAGCAGTC TGAGGAAAGT GGGGCAAGGA ATGCGCTAGT
4701  CTCTGAGGGA GACCGAGGGA GCCCCTTTCA GGAGGAGGAG GGGAGTGCTC
4751  TGAAGAGGTC TTCGGCAGGG GCTCCTGTTC ACCTGGGCCA GGGTCAGTTC
4801  CTGAAGTTCA CTCAGAGGGA AGGAGATAGA GAGTCCTGGT CCTCAGGGGA
4851  GGAC
```

Figure 4A

```
   1  MEGCMGEESF QMWELNRRLE AYLGRVKALE EQNELLSAGL GGLRRQSADT
  51  SWRAHADDEL AALRALVDQR WREKHAAEVA RDNLAEELEG VAGRCEQLRL
 101  ARERTTEEVA RNRRAVEAEK CARAWLSSQG AELERELEAL RVAHEEERVG
 151  LNAQAACAPR LPAPPRPPAP APEVEELARR LGEAWRGAVR GYQERVAHME
 201  TSLDQTRERL ARAVQGAREV RLELQQLQAE RGGLLERRAA LEQRLEGRWQ
 251  ERLRATEKFQ LAVEALEQEK QGLQSQIAQV LEGRQQLAHL KMSLSLEVAT
 301  YRTLLEAENS RLQTPGGGSK TSLSFQDPKL ELQFPRTPEG RRLGSLLPVL
 351  SPTSLPSPLP ATLETPVPAF LKNQEFLQAR TPTLASTPIP PTPQAPSPAV
 401  DAEIRAQDAP LSLLQTQGGR KQAPEPLRAE ARVAIPASVL PGPEEPGGQR
 451  QEASTGQSPE DHASLAPPLS PDHSSLEAKD GESGGSRVFS ICRGEGEGQI
 501  WGLVEKETAI EGKVVSSLQQ EIWEEEDLNR KEIQDSQVPL EKETLKSLGE
 551  EIQESLKTLE NQSHETLERE NQECPRSLEE DLETLKSLEK ENKRAIKGCG
 601  GSETSRKRGC RQLKPTGKED TQTLQSLQKE NQELMKSLEG NLETFLFPGT
 651  ENQELVSSLQ ENLESLTALE KENQEPLRSP EVGDEEALRP LTKENQEPLR
 701  SLEDENKEAF RSLEKENQEP LKTLEEEDQS IVRPLETENH KSLRSLEEQD
 751  QETLRTLEKE TQQRRRSLGE QDQMTLRPPE KVDLEPLKSL DQEIARPLEN
 801  ENQEFLKSLK EESVEAVKSL ETEILESLKS AGQENLETLK SPETQAPLWT
 851  PEEINKSGGN ESSRKGNSRT TGVCGSEPRD IQTPGRGESG IIEISGSMEP
 901  GEFEISRGVD KESQRNLEEE ENLGKGEYQE SLRSLEEEGQ ELPQSADVQR
 951  WEDTVEKDQE LAQESPPGMA GVENKDEAEL NLREQDGFTG KEEVVEQGEL
1001  NATEEVWFPG EGHPENPEPK EQRGLVEGAS VKGGAEGLQD PEGQSQQVGT
1051  PGLQAPQGLP EAIEPLVEDD VAPGGDQASP EVMLGSEPAM GESAAGAEPG
1101  LGQGVGGLGD PGHLTREEVM EPPLEEESLE AKRVQGLEGP RKDLEEAGGL
1151  GTEFSELPGK SRDPWEPPRE GREESEAEAP RGAEEAFPAE TLGHTGSDAP
1201  SPWPLGSEEA EEDVPPVLVS PSPTYTPILE DAPGLQPQAE GSQEASWGVQ
1251  GRAEAGKVES EQEELGSGEI PEGLQEEGEE SREESEEDEL GETLPDSTPL
1301  GFYLRSPTSP RWTPLESRGH PLKETGKEGW DPAVLASEGL EEPSEKEEGE
1351  EGEEECGRDS DLSEEFEDLG TEAPFLPGVP GEVAEPLGQV PQLLLDPAAW
1401  DRDGESDGFA DEEESGEEGE EDQEEGREPG AGRWGPGSSV GSLQALSSSQ
1451  RGEFLESDSV SVSVPWDDSL RGAVAGAPKT ALETESQDSA EPSGSEEESD
```

Figure 4B

```
1501  PVSLEREDKV PGPLEIPSGM EDAGPGADII GVNGQGPNLE GKSQHVNGGV

1551  MNGLEQSEES GARNALVSEG DRGSPFQEEE GSALKRSSAG APVHLGQGQF

1601  LKFTQREGDR ESWSSGED
```

DNA ENCODING NESTIN PROTEIN

GOVERNMENT FUNDING

Work described herein was supported by funding from the National Institutes of Health.

RELATED APPLICATION

This application claims priority to PCT/US92/01375 filed Feb. 21, 1992 and is a continuation-in-part of U.S. Ser. No. 07/660,412, filed Feb. 22, 1991, now abandoned which is a continuation-in-part of U.S. Ser. No. 07/603,803, filed Oct. 25, 1990, now abandoned which is a continuation-in-part of U.S. Ser. No. 07/201,762, filed Jun. 2, 1988 and now abandoned, which is a continuation-in-part of U.S. Ser. No. 07/180,548, filed Apr. 12, 1988 and now abandoned.

BACKGROUND

Brain tumors are a leading cause of cancer deaths in people under the age of 35. An important concept in our understanding of brain tumors is that the neoplastic cells may arise from undifferentiated neuroectodermal cells (Rubinstein, L. J. *J. Neurosurg* 62: 795-805 (1985)).

At the gastrula stage of central nervous system (CNS) development, neuroectoderm, forming the neural plate is derived from ectoderm which has been induced by underlying mesoderm. (Spemann, H. *Yale University Press* 1938)). The neural plate then folds, in the process called neurulation, to form the neural tube. The cells of the neural tube are the precursors for the major differentiated cell types in the central nervous system: astrocytes, oligodendrocytes, and the various types of neuron (Sauer, F. C. *J. Comp. Neurol.* 62: 377-405 (1935)). The cells of the neural tube may also be the precursors to neoplastic cells which form brain tumors.

Recent success in "tagging" individual CNS precursors and their daughter cells, either through infection by a marker-bearing retrovirus or by injection of stable, specific dyes and enzymes, has shown that neurons and non-neuronal cells (i.e., glia cells) are often derived from a common precursor. In retina a common precursor for neurons and the Mueller glial cell exists very late in development (Holt, C. E., T. W. Bertsch et al., *Neuron* 1: 15-26 (1988); Turner, D. L. and C. L. Cepko, *Nature* 238: 131-136 (1987); Wetts, R. and S. E. Fraser, *Science* 239: 1142-1145 (1988); a common precursor for different neuronal and glial cell types has also been demonstrated in cortex and tectum (Luskin, M. B., A. L. Pearlman et al., *Neuron* 1: 635-647 (1988); Price, J. and L. Thurlow, *Development* 104: 473-482 (1988); Walsh, C. and C. Cepko, *Science* 241: 1342-1345 (1988)).

Tissue culture systems have provided additional information about the differentiation potential of CNS stem cells. Single-cell microculture of embryonic day 14 rat forebrain has produced clones containing both neurons and glia (Temple, S. *Nature* 340: 471-473 (1989)). Analysis of a later precursor in the glial differentiation pathway has established specific factors influencing differentiation to oligodendrocytes or type II astrocytes (Raff, M *Science* 243: 1450-1455 1989)). Cell lines established by immortalization of CNS stem cells also reflect features of the stem cell and can differentiate along both the neuronal and glial pathways (Cepko, C. L. *Ann. Rev. Neurosci.* 12: 47-65 (1989); Frederiksen, K. et al., supra (1988)).

Antibodies have also proven useful for analyzing stem cells. For example, antibodies A2B5 (Raff, M. C. supra 1989) D1.1 (Levine, J. M., L. Beasley et al., *J. Neurosci* 4: 820-831 (1984), Rat 401 (Hockfield, S. and R. McKay, *J. Neurosci* 5: 3310-3328 (1985), and antisera against the intermediate filament vimentin (Bignami, A., T. Raju et al *Dev. Biol* 91: 286-295 (1982); Federoff, S. *Molecular Bases of Neural Development* (1985); Tapscott, S. J., G. S. Bennett et al., *Dev. Biol.* 86: 40-54 (1981) bind to antigens enriched in the proliferative zone of the neural tube. However, A2B5 and D1.1 recognize glycolipid epitopes and are less useful for analysis of gene expression. Vimentin, which appears transiently in brain development, is an ambiguous marker largely because of its promiscuous expression in many cultured cells as well as in a variety of developing and differentiated tissues (Traub, N. *Intermediate filaments: a review*. Berlin, SpringerVerlag (1985)).

The correlation between Rat 401 and proliferating cells in the developing nervous system has been examined in detail. Rat 401 was found to recognize a transient population of embryonic columnar epithelial cells and radial glial cells in many regions of the CNS (Hockfield, S. and McKay *J. Neurosci.* 5: 3310-3328 (1985)). The number of Rat 401 positive cells, their proliferative rate, and the developmental kinetics of Rat 401 expression relative to neuronal differentiation revealed that the immediate precursors to neurons are also Rat 401 positive (Frederiksen and McKay, J. *J. Neurosci* 8: 1144-1151 (1988)). Neither neurons nor glia in the adult brain express the epitope recognized by the Rat 401 antibody.

Although "tagging", tissue culture systems and antibodies have proven useful in analyzing neural precursor cells, there is still an incomplete understanding of the lineage of tumor development. For example, medulloblastoma, a common brain tumor of children, is associated predominantly with the cerebellum and brain stem. Medulloblastoma tumors contain cell types with differentiated characteristics of neurons, glia and muscle (Rubinstein, supra 1985; Coakham H. B., et al., *J. Clin. Pathol.* 38: 165-173 (1985); Velasco, M. E. et al., *Surg. Neurol.* 23: 177-182 (1985); Hayashi, K. et al., *Acta Pathologica Japonica* 37: 85-96 (1987); Cras, P. et al., *Acta. Neuropathol* 75: 377-384 (1988)).

Because of the presence of multiple differentiated cell types found in these tumors, Bailey and Cushing (Bailey, P. and H. Cushing, *Arch. Neurol. Psychiatry* 14: 192-224 (1925) proposed that rather than being multiple coincident tumors, they were derived from a multipotential stem cell, which they called a "medulloblast". According to this model, a medulloblastoma tumor would result from uncontrolled proliferation and differentiation of the medulloblast. However, the hypothetical medulloblast has not been identified.

Due to the incomplete understanding of brain tumor development, there is currently no adequate assay for detecting brain tumors at an early stage in their development. In addition, there is no specific noninvasive method of treating brain tumors. Methods of detecting and treating brain tumors would be very useful.

SUMMARY OF THE INVENTION

The present invention relates to a gene encoding a protein whose expression distinguishes neural multipotential stem cells and brain tumor cells from the more differentiated neural cell types (e.g. neuronal, glial and muscle cells) of the mammalian brain.

The present invention relates to the nestin gene, particularly a nestin gene of mammalian origin, and the encoded nestin protein. As described herein, two nestin genes of mammalian origin, the rat nestin gene and the human nestin gene, have been isolated and sequenced. The coding sequence of the rat nestin gene transcript is 5415 bp, which corresponds to an expected molecular weight of approximately 200 kD for the nestin protein. The relative molecular weight of the nestin protein as determined by SDS polyacrylamide gels is approximately 240 kD. The predicted amino acid sequence of the rat nestin gene product shows that nestin defines a distinct sixth class of intermediate filament protein.

The present invention also relates to the human nestin gene and the encoded human nestin protein. The coding sequence of the human nestin gene transcript is 4854 bp. The predicted amino acid sequence is 1618 amino acids in length, and shows significant sequence homology with the rat nestin sequence.

The present invention further relates to methods of detecting the expression of nestin as a means of diagnosing a predisposition to the development of a brain tumor or the presence of a brain tumor in an adult individual. In one embodiment, DNA present in a sample from the brain of an adult individual is hybridized to a DNA probe which is complementary to all or a portion of the nestin gene. As used herein, the term the nestin gene includes the human nestin gene whose sequence is represented herein, the rat nestin gene whose sequence is also represented herein and equivalent genes from other species, such as those which are substantially homologous to the human or the rat gene sequence. Detection of hybridization is an indication of a predisposition to the development of a brain tumor or the presence of a brain tumor. In another embodiment, cerebral spinal fluid or a serum sample from the brain of an adult individual can be stained with anti-nestin antibodies. Detection of stained cells is an indication of a predisposition to the development of a brain tumor or the presence of a brain tumor.

BRIEF DESCRIPTION OF THE DRAWINGS

FIG. 1A–1H is the nucleotide sequence of rat nestin (SEQ ID NO: 1).

FIG. 2 is the deduced amino acid sequence of rat nestin (SEQ ID NO: 2).

FIG. 3A–3D is the nucleotide sequence of human nestin (SEQ ID NO: 3).

FIG. 4A–4B is the deduced amino acid sequence of human nestin (SEQ ID NO: 4).

DETAILED DESCRIPTION OF THE INVENTION

The present invention relates to a gene of mammalian origin encoding a protein whose expression distinguishes neural multipotential stem cells and brain tumor cells from the more differentiated neural cell types (e.g., neuronal, glial and muscle cells of the adult brain).

The present invention more particularly relates to the nestin gene and the encoded proteins and their use in diagnosing tumors of the brain, such as medulloblastomas, gliablastomas and oligodendroglioma. As described herein, the human nestin gene and the rat nestin gene have been isolated and sequenced. In addition, expression of the nestin gene and its structural features are described. The intracellular distribution of the nestin gene product, both in an embryonic rat brain cell line (ST15A) and human brain tissue, including tumor cells, using immunocytochemical and immunohistochemical techniques is also described. Finally, nestin expression in the developing human central nervous system and brain tumor samples is also described herein.

CLONING AND CHARACTERIZATION OF THE RAT AND HUMAN NESTIN GENE

The Rat Nestin Gene

A cDNA library in the expression vector lambda gt11 was constructed from poly(A)+ RNA from CNS of embryonic day 15 (E15) rat embryos as described in detail in Example 1. The library was screened with the monoclonal antibody Rat 401 after induction of protein expression and immunopositive plaques were identified. The cDNA insert from the most immunopositive clone, gt11.401.19, was used as probe to isolate additional clones, gt10,401:16, gt10,401:18 and gt10.401:9, in a lambda gt10 library from rat E15 CNS constructed in parallel with the gt11 library. A number of hybridizing clones were identified and sequenced and together represent 5333 base pair (bp) of transcribed sequence, including 404 bp of 3' untranslated sequence and a consensus polyA addition site.

The remaining portion of the nestin gene was obtained from genomic sequences. Genomic Southern blots, even when hybridized at low stringency, revealed a pattern consistent with a single rat gene. A genomic rat library in the vector Charon 4A was screened with the nestin cDNA clones. Hybridizing clones were organized by restriction mapping and the region upstream of the cDNA clone gt10.401:9 was sequenced.

An open reading frame continues for an additional 600 bp from the 5' end of the most upstream cDNA clone. This region from the genomic clone Cha.401:14 was subdivided into three different fragments with the restriction enzyme BamH1. These three fragments all hybridized to an mRNA of the correct size, 6.2 kb, when used as probes on Northern blots with rat E15 CNS RNA.

The exact location of the 5' end was determined by a combination of S1 nuclease mapping and primer extension. A probe (bp −121 to +194 relative to +1= the subsequently defined transcription start) was generated overlapping the end of the genomic open reading frame by polymerase chain reaction between two specific primers. This PCR product protected a 194 bp fragment in S1 nuclease analysis. Primer extension from the downstream primer used to generate the PCR fragment also produced a 194 bp fragment. The fact that these two experiments gave the same fragment suggests that the transcription start site has been defined.

FIG. 1A–1H shows the nucleotide sequence of the rat nestin gene (SEQ ID NO: 1). The total length of the rat nestin gene is 11,236 base pairs (bp). The total length of the nestin gene transcript is 5945 bp, excluding the poly A tail. There are two potential initiation codons at positions +127 and +160. Assuming the first methionine is the initiation codon, the coding sequence is 5415 bp. FIG. 2 shows the deduced amino acid sequence (SEQ ID NO: 2) encoded by the rat nestin gene, which is 1805 amino acid residues in length. This corresponds to a protein of an expected molecular weight of approximately 200 kD; the relative molecular weight as determined by migration on SDS polyacrylamide gels is approximately 240 kD (Hockfield and McKay, supra (1985)). Sequence comparison of cDNA and genomic clones reveals three introns at positions 912, 1038, and 1111 in the transcribed region.

To confirm that the cloned gene indeed represents the gene encoding the Rat401 antigen, a synthetic peptide from the C-terminal 20 amino acids was made. The extreme C-terminus was chosen because it is not included in the clone recognized by the original monoclonal antibody, and therefore represents a distinct epitope. A polyclonal antiserum against the peptide was raised in rabbits and identifies a band in Western blots and a pattern in immunostaining experiments which are indistinguishable from that recognized by the monoclonal antibody Rat 401.

Structural Features of the Rat Nestin Gene

The sequence of the entire transcribed region of the rat nestin gene was compared to the Genbank and EMBL databases. The only significant similarities found are to the five classes of intermediate filaments: acidic keratins (class I); basic keratins (class II); desmin, glial fibrillary acidic protein, peripherin, and vimentin (class III); the neurofilament triplet (class IV); and nuclear lamins (class V) (Steinert and Roop, 1988)).

The similarity between the nestin gene and the genes of the other five classes of intermediate filaments ranges from 16 to 29% at the amino acid level in a 307 amino acid long region starting close to the N-terminus of the nestin gene, corresponding to the conserved alpha-helical rod or "core" domain of the intermediate filaments. This region of the predicted nestin amino acid sequence also contains a repeated hydrophobic heptad motif characteristic of intermediate filaments. The degree of amino acid similarity is comparable to that found between different classes of intermediate filament, both in degree and in location, i.e., conserved heptad-containing alpha-helical stretches within the core domain are separated by less well conserved, non-heptad spacers (Steineft, P. M. and D. R. Roop, Ann. Rev. Biochem. 57: 593–625 (1988)). The locations of the nestin gene's three introns are not conserved with respect to those of other classes of intermediate filaments.

In the regions outside the conserved rod domain, no strong similarities to other characterized genes were found. The N-terminal domain is only 11 amino acid residues long, shorter than in other intermediate filaments. The large C-terminal domain loosely resembles those of neurofilaments in that it is highly charged, bears glutamate-rich regions, and features a repeat, in this case the 11 amino acid motif S/P-L-E-E/K-E-X-Q-E-S/L-L-R (underlined residues are strongly conserved). There are approximately 35 of these repeats in the region between amino acids 512 and 1050.

The deduced amino acid sequence (SEQ ID NO: 2) of nestin suggests that it is a member of the intermediate filament protein family. However, its degree of sequence homology to other intermediate filaments in the core domain, its dissimilarity in the head and tail domains, and its different splicing pattern suggest that it defines a new class of intermediate filament protein.

The Human Nestin Gene

As described in detail in Example 5, the human nestin gene was isolated using low stringency DNA hybridization of a human genomic bacteriophage lambda library with a rat nestin probe.

FIG. 3A–3D shows the nucleotide sequence of the human nestin gene (SEQ ID NO: 3). The total length of the human nestin gene sequence is 4854 bp. FIG. 4A–4B shows the deduced amino acid sequence (SEQ ID NO: 4) encoded by the human nestin gene which is 1618 amino acid residues in length. The alignment of the deduced amino acid sequences of human nestin with the deduced amino acid sequence of rat nestin showed greater than 75% sequence similarity between the two sequences, with greater than 60% sequence identity.

DEVELOPMENTAL EXPRESSION OF THE RAT AND HUMAN NESTIN GENE AND ENCODED PRODUCT

Developmental Expression of the Rat Nestin Gene

During development, CNS stem cells differentiate into neurons and glia on a stereotyped schedule; different brain regions become post-mitotic at different times. The nestin protein was originally identified by the Rat 401 antibody, which transiently stains radial glial cells of the neural tube in cross sections of rat embryos (Fredericksen, K. and R. McKay, J. Neurosci 5: 3310–3328 (1988); Hockfield and McKay, supra (1985)). The distribution of staining in the neural tube at different developmental stages, combined with quantitative double-label experiments using tritiated thymidine autoradiography and FACS cell cycle analysis, showed that expression of the Rat 401 antigen was localized to proliferating CNS stem cells during embryogenesis (Frederiksen and McKay, supra (1988)) and U.S. patent application Ser. Nos. 180,548, abandoned; 201,762, abandoned and 603,803, abandoned herein incorporated by reference. These experiments have been extended by analyzing the developmental expression of the nestin gene.

Northern blots of RNA from E15 rat CNS or from the Rat 401 positive cell line ST15A were probed with nestin cDNA inserts, a single 6.2 kb mRNA species was identified. To investigate the temporal profile of nestin RNA expression in the developing CNS, representatives of early (cerebrum) and late (cerebellum) developing regions of the brain were compared.

In cerebrum, nestin expression was found to decline from a maximum on day E16, such that only extremely low levels of RNA could be detected at day P9 and P12 and none at all in the adult cerebral cortex, even after long exposures. The loss of nestin mRNA precisely parallels the decline of Rat 401 positive stem cells in cerebrum during neurogenesis (Frederiksen and McKay, supra (1988)). The postnatal cerebellum expresses the nestin gene with a maximum on day P5; no expression can be detected after day P9. Again, this pattern closely matches the numbers of Rat 401 positive cells in developing cerebellum.

Nestin is not detected by Northern blot analysis in adult tissue. The loss of nestin expression coincides with terminal differentiation of these early multi-potential cells. There are two important implications of these results. First, nestin appears to be a general marker for the CNS stem cell from the newly closed E11 neural tube through the postnatally developing cerebellum. Second, nestin expression is a consequence of transcriptional regulation of the gene.

The only expression of nestin observed outside developing CNS is traces of nestin message from day P4 developing skeletal muscle. This finding is consistent with previous observations from cross sections of rat embryos, where Rat 401 staining in the developing somites was observed (Hockfield and McKay, supra (1985)). Developing nervous tissue and developing skeletal muscle may share unexpected kinship with regard to their potential fates.

Intracellular Distribution of the Nestin Gene Product in the ST15A Cell Line The associations of nestin with different components of the cytoskeleton were analyzed by a series of double-label immunocytochemistry experiments. These experiments were carried out in the immortalized CNS precursor cell line ST15A which expresses, in addition to components of microtubules and microfilaments, nestin and the intermediate filament vimentin. ST15A produces a nestin mRNA indistinguishable by Northern blot analysis from that found in E15 CNS.

In the first set of double-label experiments the intracellular distribution of the nestin gene product, detected by the monoclonal Rat.401 antibody and an appropriate second antibody, was compared to the distribution of actin, tubulin and vimentin. The latter two proteins were detected by polyclonal antibodies with matching second antibodies while the actin pattern in microfilaments was visualized by rhodamine-conjugated phalloidin.

The intracellular distributions of nestin, microtubules (tubulin), and microfilaments (actin) are quite different. Microtubules are more evenly distributed in the cell with no particular aggregation around the nucleus, whereas nestin is found in a fiber-like pattern, with a pronounced perinuclear accumulation. We also observe distinct differences when microfilaments and nestin are stained in the same cell: microfilaments form straight and parallel fibers, in contrast to the gently curved fibers of nestin.

Differences in nestin and vimentin staining in the same ST15A cells are much less clear. Vimentin staining is stronger than nestin in the cell periphery, and there are regions where intensity varies between the two proteins, but common features are also evident. The overall organization of the two networks is quite similar, with filament arrays radiating out from a perinuclear center. Moreover, there are regions in cells where it seems likely that nestin and vimentin colocalize.

In another set of experiments, microfilaments and microtubules were disrupted by cytochalasin B and colchicine, respectively, and the effects on nestin distribution analyzed. When ST15A cells were treated with 10 ug/ml cytochalasin B for one hour the microfilaments became highly disorganized, while the overall morphology of the nestin network was preserved. Microtubules also remained intact after the cytochalasin B treatment. Colchicine treatment (25 ug/ml) for 24 hours caused a collapse of the microtubules. The nestin network could still be identified, although the perinuclear distribution became much more prominent. A similar pattern was observed for vimentin as has been previously reported (Hynes, R. O. and A. T. Destree, *Cell* 13:151-163 (1978): Monteiro, M. J. and D. W. Cleveland, *J. Cell Biol.* 108: 579-593 (1989). Microfilaments were essentially unaffected by the colchicine treatment. The inferred relationship of nestin to intermediate filaments based on its deduced amino acid sequence is thus supported by the intracellular distribution of the nestin gene product under various conditions.

ST15A Cells have Features Expected of a Neural Precursor to Brain Tumors

"The prevailing name 'medulloblastoma' given by Bailey and Cushing (1925), is unfortunate because there is no embryonal cell that has been identified as a medulloblast." This sentence begins the discussion of medulloblastoma in a prominent text on neural tumors (Russell, D. and L. J. Rubinstein, *Pathology of Tumors of the Nervous System,* Baltimore, Williams and Wilkins (1989)). The following presents evidence that a cell line derived from rat cerebellum, ST15A, has features expected of a medulloblast.

ST15A was derived from postnatal day 4 rat cerebellum. In the rat, as in other mammals, much of cerebellar development occurs after birth, so that there are a large number of dividing precursor cells present at the time from which this line was derived. Thus, ST15A is derived from the appropriate tissue and stage of development. It has previously been shown that ST15A cells can differentiate along neuronal and glial pathways. The following experiments, which are described in detail in Example 3, show that ST15A cells can also differentiate into muscle. This result suggests that a single neuroectodermal cell can give rise to the different cell types found in brain tumors.

The cerebellar cell line ST15A was one of several cell lines obtained by infecting primary rat cerebellar cells with a recombinant retrovirus carrying SV40 T-antigen. A temperature sensitive allele of T-antigen was used to establish these cell lines. At the permissive temperature (i.e., when the T-antigen protein is active) the cells proliferate and express the intermediate filament protein nestin.

At the non-permissive temperature the T-antigen protein is rapidly degraded and the cells differentiate into either neurons or glial cells depending on the conditions. The differentiation into neurons and glial cells is best accomplished by growing ST15A cells in co-culture with primary cerebellar cells. Partial differentiation has also been observed when ST15A cells are cultured alone; serum-free medium promotes neuronal differentiation and medium containing fetal calf serum promotes glial differentiation.

ST15A cells also can differentiate into muscle cells. This fate was first noted when spontaneously contracting cells were observed in long term cultures of ST15A at 39° C., the non-permissive temperature for T-antigen. Horse serum is often used to support the differentiation of primary myoblasts. When ST15A cells are grown in horse serum at 39° C., they reproducibly differentiate into multi-nucleate cells which express muscle specific proteins, regenerative action potentials and spontaneously contract.

ST15A cells grown for two days at 33° C. in 10% fetal calf serum (FCS) in DMEM grew in a disorganized manner; in contrast ST15A cells grown at 33° C. in 10% horse serum at 39° C. became aligned. The monoclonal antibody Rat 401 recognizes the 220 kD intermediate filament protein nestin. ST15A cells express nestin at both 33° C. and 39° C. A second monoclonal antibody which recognizes a skeletal and cardiac muscle isotype of troponin T was reacted with the cells (Lin, *J. Biol. Chem.* 263: 7309 (1988)). Immunofluorescence shows that troponin T expression is induced when ST15A cells are cultured at 39° C. in horse serum.

Immunoblots of proteins extracted from ST15A cells verify that anti-troponin T antibody recognizes a strong band of 38 Kd, the appropriate molecular weight, in the cells grown at 39° C. in horse serum; at 33° C. no band is present. The troponin band in ST15A co-migrates with troponin extracted from rat postnatal day 4 muscle. The double band seen in both muscle cells and differentiated ST15A cells may represent the adult and embryonic isoforms of troponin T which differ by 3,000 daltons (Lin, J. Biol. Chem. 263: 7309 (1988)). These two isoforms are derived from the same primary transcript by differential splicing. Lanes carrying the same amount of protein were also probed for nestin with the monoclonal antibody Rat 401. Nestin is present at both temperatures but at elevated levels at the higher temperature. The lower bands are proteolytic fragments of nestin which are often present in protein extracts even in the presence of protease inhibitors. Nestin is also present in postnatal rat muscle.

A family of DNA binding factors has been shown to play a critical role in the differentiation of muscle. These proteins, myoD1, myogenin, myf5 and herculin/MRF4, contain DNA binding motifs of the helix-loop-helix type in a region of homology to c-myc (Wright, W. E., et al., Cell. 56: 607 (1989); Miner, J. H. and B. Wold, Proc. Nat. Acad. Sci. 87: 1089–1093 (1990); Davis, R. L. et al., Cell. 51: 987–1000 (1987); Braun, T et al., EMBO J 8: 701–709 (1989); Rhodes S. J. and S. F. Konieczny, genes and dev. 3: 2050–2061 (1989). The expression of these factors at the mRNA level in ST15A cells as they differentiate into muscle was examined.

Northern blot analysis of total RNA from differentiating ST15A cells probed with the indicated sequences was performed. Each probe hybridized only to the bands of the expected mobilities. MyoD1 is expressed in passaging ST15A cells at the permissive temperature for the T antigen and continues to be expressed when the cells are shifted to 39° C. Myogenin is not expressed under normal growth conditions but is expressed by 2 days after confluent cells are shifted to 39° C. in horse serum (HS); if confluent cells are placed in HS and held at 33° C., the induction of myogenin expression is dramatically inhibited.

Herculin/MRF4 was found in adult skeletal muscle but was not detected in ST15A. Myf5 gave a very weak signal in ST15A cells compared to the myoblast cell line C2C12. Nestin mRNA accumulates with time at 39° C., as does the protein. b-actin serves as a control for the amount of RNA at 33° C. and in the short time points at 39° C.; the decrease in b-actin signal at 3 and 7 days at 39° C. may be due to the changing composition of the cytoskeleton accompanying differentiation, as levels of myoD1 mRNA appear constant throughout the experiment. These results indicate the ST15A cells express myogenic transcription factors and that the induction of myogenin correlates with the differentiation into the muscle fate.

As expected of muscle cells, ST15A cells become multinucleate as they differentiate. The most striking similarity to muscle, which initiated this series of experiments, was that ST15A cells grown to confluence in FCS at 33° C. and cultured for up to 15 days at 39° in 10% horse serum can contract spontaneously. The initial action potentials were generated by a series of hyper-polarizing pulses. The final hyper-polarizing pulse was followed by a train of spontaneous action potentials. Spontaneous action potentials were seen after 12 days at 39° C. in 10% horse serum.

Coincident with the appearance of contracting cells, the resting membrane potential falls and it becomes easier to stimulate trains of action potentials with hyper-polarizing current pulses. ST15A cells also twitched in response to stimuli which elicited action potentials. These results show that ST15A cells differentiate into muscle, expressing myogenic transcription factors, muscle-specific cytoskeletal components and electrical excitability.

An interesting question raised by the properties of ST15A cells is whether primary cerebellar cells can differentiate into the muscle fate. Dissociated cells from postnatal day 5 rat cerebellum were cultured for 6 days under conditions which promote muscle differentiation of ST15A cells (39° C. in the presence of 10% horse serum) and stained with monoclonal antibody against troponin T. These culture conditions promote extensive differentiation of neurons and glia. Troponin T positive cells with an elongated, multinucleate morphology of muscle cells were also seen, but these cells were very rare, occurring less than one per hundred thousand cells.

Developmental expresssion of Human Nestin Gene

To characterize human nestin and determine the timing of its induction in the normal human developing CNS, studies were carried out, to examine this class VI IF protein in the normal human developing central nervous system (CNS), human brain tumor derived cell lines, and tissue samples of human CNS tumors.

Human nestin exhibited biochemical and immunochemical properties similar to those of rat nestin. Further, in the human, nestin was detected immunohistochemically in several different types of immature human CNS cells, i.e. germinal matrix cells, neuroepithelial cells lining the central canal, radial glia and endothelial cells. Nestin appeared in these cells at the earliest gestational age (i.e., 6 weeks) examined here and then it declined in all but the endothelial cells at later embryonic stages. Nestin also was detected by immunocytochemistry in 6 of 7 primitive neuroectodermal tumor cell lines and in both of the malignant glioma cell lines examined. In these cell lines, nestin co-localized incompletely with bundles of IFs containing other IF proteins (i.e. vimentin, glial filament, nuerofilament). Nestin was ubiquitous in a wide variety of brain tumors, but was most prominent in gliomas. These studies document the existence of a human counterpart of rat nestin.

Distribution of the Nestin Gene Product in the Human Developing CNS

Cervical levels of six developing human spinal cords with gestational ages (GAs) of 6 to 40 weeks were immunohistochemically stained with anti-nestin 129. The spinal cord of the 6 weeks GA human fetus was composed of three distinct layers, i.e. a layer of primitive neuroepithelial cells lining the central canal, a mantle layer and an outer marginal layer. Anti-nestin 129 stained most cells in the primitive neuroepithelial layer, i.e. the presumptive miltipotential stem cells that give rise to CNS neurons and glia. In addition, thin elongated radial glial fibers extending from the primitive neuroepithelial layer to the subpial region were stained by this antiserum. These neuroepithelial stem cells and radial glial fibers also expressed vimentin but not GFAP. Neuroblasts in the mantle layer (identified by their morphology and NF protein positively) did not express nestin.

At 11 weeks GA, cells in the ependymal layer were positively stained with anti-nestin 129, as were radial glial fibers. These radial glial fibers were also stained with the anti-vimentin MAb. Nestin immunoreactivity decreased at 17 weeks GA and disappeared at 20 weeks GA. From this gestational age to maturity, GFAP positive glial cells and NF positive neurons were seen in the spinal cord, but no elements other than endothelial cells were nestin positive.

The telencephalic germinal matrix of two cases with GAs of 17 and 20 weeks were examined with anti-nestin 129. At both time points, many presumptive neuroepithelial stem cells in the germinmal matirx cells were nestin positive. These neuroepithelial precursor cells also were labeled by the anti-vimentin MAb, but no germinal matrix cells were stained by the MAbs to GFAP or NF proteins. At 40 weeks GA, a well defined germinal matrix was not evident, but clusters of morphologically immature cells (presumably residual, multipotential precursor cells) were seen in the subependymal region. Nestin immunoreactivity was recognized in only a few of these cells.

To determine if neuroepithelial precursors in the cerebellum also expressed nestin, four developing human cerebelli at GAs of 17 to 40 weeks were studied. Late in development, the cerebellar cortex has four distinct layers, i.e. the internal and external granular layers, the Purkinje cell layer and the molecular layer. However, these layers were not yet evident at 17 weeks GA and Purkinje cells were not recognizable by morphological criteria. Nevertheless, immature NF positive cells were observed at 17 weeks GA in the superficial internal granular layer, and these cells probably correspond to nascent Purkinje cells. Nestin immunoreactivity was detected at this time in radial glial cells in the internal granular layer and in radial glial processes that extended to the external granular layer. These radial glial cells, which mature into the Bergmann glia of the adult cerebellum, also were stained by the antivimentin MAb (data not shown), but not by the anti-GFAP MAb. However, the anti-GFAP MAb did stain ependymal cells lining the fourth ventricle. At 20 weeks GA, nestin immunoreactivity in radial glia was markedly diminished and by 40 weeks GA, it was weakly present in only a few radial glia fibers, while the blood vessel endothelial cells at 40 weeks GA were clearly nestin positive. In contrast, radial glial fibers expressed both GFAP and vimentin (data not shown) at these time points.

Nestin Expression in Brain Tumor-derived Cell Lines

Indirect immunofluorescence studies of 9 well characterized human brain tumor derived cell lines showed variable nestin immunoreactivity in 6 of 7 primitive neuroectodermal tumor (PNET) cell lines, and very intense nestin staining in 2 glioma cell lines. Table 1 summarizes the data on the expression of nestin and other IF proteins in these cell lines.

TABLE 1

| CELL LINES | IMMUNOFLUORESCENCE ASSAY OF BRAIN TUMOR-DERIVED CELL LINES | | | | | |
|---|---|---|---|---|---|---|
| | NESTIN | VIMENTIN | GFAP | NF-L | NF-M | NF-H |
| Daoy | − | + | − | − | − | − |
| D283 Med | + | + | − | + | + | + |
| D341 Med | + | + | − | − | + | + |
| D384 Med | + | + | − | + | + | + |
| D425 Med | + | + | − | + | + | + |
| D458 Med | + | + | − | + | + | + |
| CHOP707m | + | + | − | + | − | − |
| U251 MG | + | + | + | − | − | − |

Summary of the data obtained from the indirect immunofluorescence studies of each cell line. The patterns of staining are described as
− = no staining,
+ = positive staining.
NF-L, NF-M and NF-H are the low, middle and high molecular weight neurofilament subunits, respectively.
The following antibodies were used to obtain these data;
nestin (rabbit anti-nestin antiserum 129),
vimentin (V9),
GFAP (2.2B10),
NF-L (NR-4, RMS12),
NF-M (RMdO20, RMO254, HO14),
NF-H (DP1, TA51, RMO24).

Except for CHOP707m, which was derived from a cerebral neuroblastoma (Baker, D. L. et al., Am. Neurol. 28:136 (1990)), the other 6 PNET cell lines were obtained from cerebellar medulloblastomas (see Hockfield, S. et al., J. Neurosci 5:3310 (1985)) and citations therein). Daoy does not exhibit any evidence of glial or neuronal differentiation and it was nestin negative, while the other 6 PNET cell lines resembled that of embryonic neuroblasts (He, X. et al., J. Neuropathol. Exp. Neurol. 48:48 (1989)). Double immunofluorescent staining of D283 Med, which is the most differentiated PNET cell line, showed incomplete co-localization of nestin and NF proteins in bundles of IFs in the same cells. Similar observations were made using nestin and vimentin antibodies. CHOP707m expressed extensive nestin immunoreactivity and double immunofluorescence of nestin and vimentin in this cell line co-localized both proteins in the same cells, but the nestin positive filament bundles were located mainly in the perinuclear area while vimentin positive filament bundles were present throughout these cells. The Daoy line expresses vimentin, but not NF proteins, GFAP or other molecular markers of neurons or glia (He, X. et al., J. Neuropathol. Exp. Neurol. 48:48 (1989)). Hence, Daoy is the least differentiated PNET cell line, and it did not express nestin. The foregoing co-localization studies also indicated that the anti-nestin 129 did not cross react with vimentin or NF proteins.

Since nestin is expressed primarily in CNS stem cells and is eliminated during the progressive maturation of the progeny of these stem cells, the Daoy cell line may resemble a CNS precursor that subsequently develops into a vimentin and nestin positive CNS stem cell like those observed here in the human spinal cord at a GA of 6 weeks. Alternatively, tumor cell lines contain genetic mutations and their phenotype may not fully replicate that of normal cells. However, the 2 glioma cell lines (U251 MG and U373 MG) resembled immature spinal cord radial glia (i.e. at 11 weeks GA) since these cells co-expressed nestin, GFAP and vimentin in the triple fluorescence studies.

Finally, Western blot studies were performed which showed that anti-nestin 129 labeled a single band in cytoskeletal extracts of U251 MG cells, and this immunoband had a $M_r$ similar to that of the bacterial TrpE-nestin fusion protein and lower than that of rat nestin expressed in P6 rat cerebellum. The significance of the difference in the $M_r$ of rat and human nestin is unclear and will require further studies. Since these extracts contained vimentin, GFAP and other cytoskeletal proteins, these data further demonstrate the specificity of the anti-nestin antiserum for human nestin.

THE EXPRESSION OF NESTIN IN BRAIN TUMOR TISSUE

Brain Tumors Contain Nestin Positive Cells

ST15A cells express properties expected of the precursor to brain tumor cells as described in Example 3. Therefore, brain tumor cells were tested to determine whether they express features in common with ST15A, such as expression of nestin. As described in detail in Example 6, tissue from five medulloblastomas was obtained. Three of these samples came from recurrent tumors occurring in a 16 year old male, a 26 year old male and a 5 year old female. The remaining tumors were newly diagnosed in an 11 year old male and a 10 year old female. The primary tumor in the 11 year old male was also used as a source of cultured cells.

Immunohistochemistry on sections of tissue from each of the five tumors studied showed regions with large numbers of nestin immunoreactive cells. The expression of nestin in medulloblastoma tissue was not uniform and in some cases parts of the tumor tissue showed a few nestin-positive cells among nestin-negative cells. The pre-immune serum showed no reaction with either human embryonic or tumor tissue. The nestin positive cells were small with a cytoplasmic distribution of the antigen. In one tumor, there were groups of aligned nestin positive cells which were very similar in their morphology to the embryonic neuroepithelium.

A cell line which was generated by growing cells out of the medulloblastoma from the 11 year old male was also tested for expression of nestin. Immunocytochemistry with polyclonal anti-nestin antiserum shows that these cells are uniformly positive for nestin expression and reveals the filamentous pattern characteristic of this intermediate filament protein. Western blotting using anti-nestin serum shows that the antigen detected in these cells comigrates with rat nestin.

Sections of normal fetal and adult human cerebellum were also stained with polyclonal antiserum against nestin. The fetal tissue showed many positive cells in the proliferative, external granular layer of the developing cerebellum and in the outer part of the internal granular layer. In contrast, there was no immunoreactivity in cerebellum from a 2.5 year old. These results are consistent with the stem cell specific expression of nestin seen in developing mouse and rat brain.

Utility

The adult cell types of the brain express distinct intermediate filament proteins: neurofilaments are expressed by neurons, peripherin by a subset of neurons (Leonard, Gorham, et al., (1988)), and glial fibrillary acidic protein by astrocytes. The expression of nestin defines an earlier stage in the pathway of intermediate filament gene expression. Early embryonic cells are nestin negative but express certain cytokeratins (Jackson, B. W., C. Grund et al., *Differentiation* 20: 203–216 (1980)). During neurulation neurectodermal cells become nestin positive. Upon terminal differentiation, CNS cells stop producing nestin and express class III or IV intermediate filaments typical of their differentiated cell type.

Nestin positive neurectodermal cells have been shown to be capable of differentiating into neuronal, glial and muscle cells (i.e., the different cell types found in tumors). Nestin expression has also been directly detected in tumor tissue and in a medulloblastoma derived cell line. Nestin positive cells derived from tumors are likely to be renewing stem cells which give rise to the differentiated cells in the tumor.

The detection of nestin expression in brain cells obtained from an adult using known methods is indicative of the presence of a brain tumor or of neural precursor cells capable of developing into a brain tumor. For the purposes of the subject invention, an "adult" is an individual whose central nervous system is developed and, therefore, contains differentiated cells. For example, the central nervous system of human neonates is in continual development up until the age of about one year. Therefore, a human adult, for the purposes of the subject invention, is an individual who is older than about one year.

Nestin mRNA expression in a brain tissue sample can be detected using a DNA probe; this is indicative of expression of nestin, which is, in turn an indication of a predisposition to the development of a brain tumor or of the presence of a brain tumor in the individual. For example, a sample of brain tissue from of an individual can be hybridized to a DNA probe which is complementary to all or a portion of the nestin gene. Detection of hybridization is an indication of a predisposition to the development of a brain tumor or the presence of a brain tumor.

Alternatively, expression of the nestin protein can be detected using polyclonal antibodies, (e.g., anti-nestin antiserum 129) or monoclonal antibodies (e.g., Rat 401). For example, cerebral spinal fluid or a serum sample from the brain of an individual can be stained with anti-nestin antibodies. Detection of stained cells is an indication of a predisposition to the development of a brain tumor or the presence of a brain tumor.

The finding that neural precursors to tumors express nestin also has important therapeutic implications. For example, the nestin marker enables further investigation into the proliferation and differentiation of the stem cells of a brain tumor, so that existing chemotherapies can be implemented at an earlier stage in the tumor development and so that new methods of inhibiting tumor development can be developed.

The present invention will now be illustrated by the following examples, which are not to be seen as limiting in any way.

EXAMPLE 1 Cloning and Characterization of the Rat Nestin Gene

Construction and Screening of Libraries

λgt10 and λgt11 cDNA libraries were constructed from oligo-dT-primed poly(A)+RNA from embryonic day 15 dissected rat CNS according to procedures which were slightly modified from those described (Young, R. A. and R. W. Davis, *Proc. Natl. Acad. Sci. USA.* 80: 1194–1198 (1983)). The second strand cDNA was synthesized using the RNase H modification of the Okayama-Berg method (Gubler, U. and R. Hoffman, *Gene* 25: 263–269 (1983)). After induced protein expression, the λgt11 library was screened with the monoclonal antibody Rat 401 (undiluted hybridoma supernatant) and positive clones were visualized with an anti-mouse second antibody conjugated to alkaline phosphatase (Promega Protoblot). Immunopositive clones were selected and the cDNA insert from the clone giving the strongest hybridization signal, λgt11.401:16, was $^{32}$P-labelled (Feinberg, A. P. and B. Vogelstein, *Anal. Biochem.* 137: 266–267 (1983) and used as probe to screen the λ gt10 library (Benton W. D. and R. W. Davis, *Science.* 196: 180–182 (1977); Thomas, P. S. *Proc. Natl. Acad. Sci. USA.* 77: 5201–5205 (1980)). Several clones were identified. A commercial rat genomic DNA library (Clontech) in the vector Charon 4A was screened with $^{32}$P-labelled nestin cDNA inserts as above. A number of hybridizing clones were obtained, and a genomic map comprising 20 kb of the nestin gene region was established by restriction mapping of the genomic clones, cross-hybridizations, and sequencing of selected genomic subclones.

DNA Sequencing and Computer Analysis cDNA inserts and genomic subclones were sequenced after subcloning into M13mp18, M13mp19, or Bluescript KS+ (Stratagene). M13 phage particles and Bluescript were grown and circular DNA prepared according to standard procedures. Both single stranded (M13) and double stranded (Bluescript) sequencing was performed using a modified T7 DNA polymerase (Sequenase, USB), as suggested by the manufacturer. Approximately 90% of the gene, including all exons and cDNA inserts, was sequenced on both strands. Ambiguous regions were further resolved using deoxyinosine in the standard Sequenase protocol. Computer analysis was performed using the University of Wisconsin Genetics Computer Group program package, including the FASTP and TFASTA algorithms (Devereux, Haeberli et al., 1984)). The complete sequence, including introns, will be stored in the EMBL Database.

Isolation of RNA and Northern Blotting

Tissue was rapidly dissected and quickly frozen in liquid nitrogen. After homogenization in a quanidinium thiocyanate containing buffer, total RNA was isolated by centrifugation through a CsCl cushion (Chirgwin, Przybyla et al., 1979)). Poly(A)+RNA was isolated by an oligo-dT chromatography column (Aviv and Leder, 1972) or by a poly(A)+RNA extraction kit (Fast Trak, Invitrogen). For Northern blot analysis RNA was denatured and electrophoresed in 1% agarose gels containing 2.2 M formaldehyde in 1X MOPS buffer (Maniatis, Fritsch et al., 1982) at +4° C. for 8 hours. The RNA was then transferred to nitrocellulose filters (GeneScreen Plus, New England Nuclear) (Thomas, 1980)). The filters were prehybridized and hybridized (50% formamide, 0.75 M NaCl, 100 mM Tris pH 7.8, 5 mM EDTA, 1% sodium dodecyl sulphate at 42° C. for 16 hours) with $2\times10^6$ cpm/ml of the $^{32}$P-labeled nestin cDNA insert from λ gt10.401:16 (specific activity $3\times10^8$ cpm/ug). After hybridization, the filters were washed (final wash=$2\times30$ minutes at 65° C. in 30 mM NaCl, 4 mM Tris pH 7.8, 0.2 mM EDTA and 0.25% SDS) and exposed to x-ray film with intensifying screens. Quantity and integrity of the RNA were monitored by rehybridizing the blots with a cDNA probe from the human beta-tublin gene under identical conditions. The size of the hybridizing RNA was determined by running RNA molecules of known size (HMW RNA ladder, BRL) in parallel.

S1 Nuclease Mapping and Primer Extension

To generate a probe for S1 nuclease protection experiments, we amplified a region of a genomic clone between two synthetic primers using the polymerase chain reaction (kit from Perkin-Elmer Cetus). The resulting fragment was 315 bp long and located between bp −121 and +194 (bp +1 indicates the subsequently defined initiation of transcription). After $^{32}$P end-labelling, 300 fmole of the fragment was hybridized to 50 ug of E15 CNS rat total RNA or 50 ug of yeast total RNA according to standard procedures, and the S1 resistant hybrids separated on denaturing polyacrylamide gels (Maniatis, T., E. F. Fritsch et al., *Molecular cloning: A laboratory manual (Cold Spring Harbor, N.Y.:* (1982)). 32P end-labeled restriction digested plasmids and sequencing reactions of known DNAs were used as size standards. The dried gels were exposed to x-ray film. Primer extensions were performed by hybridizing 125 fmole of one of the oligonucleotides used in the polymerase chain reaction (pos +170−+194) to 10 ug of poly(A)+RNA from rat E15 CNS according to standard procedures. The reaction product was subjected to gel electrophoresis as in the S1 nuclease experiments.

Immunocytochemistry

For all experiments cells from the immortalized cell line ST15A were grown for 2 days (to 40% confluence) in Dulbecco's modified Eagle's medium supplemented with 10% fetal calf serum on sterile, polyornithine coated glass cover slips, as described in U.S. patent applications Ser. Nos 07/603,803, abandoned; 07/201,762, abandoned and 180,548, abandoned. All antibody incubations lasted 60 minutes at room temperature and were followed by three rinses in PBS (0.14 M) NaCl, 2.7 mM KCl, 8 mM $Na_2HPO_4$ and 8 mM $KH_2PO_4$ pH 7.2). In the double-lable experiments with nestin and tubulin antibodies the ST15A cells were briefly rinsed in PBS, presoaked in microtubule stabilizing buffer (MTSB=2 M glycerol, 0.1 M PIPES pH 6.9, 1 mM $MgSO_4$, 2 mM EDTA) for 2 minutes and then fixed for 5 minutes in 4% paraformaldehyde, 0.5% NP-40 in MTSB for 5 minutes. After two brief rinses in PBS and 5 minutes incubation in blocking solution (0.75% Triton X-100, 500 ug/ml bovine serum albumin, 1% horse serum and 0.05% sodium azide), the cells were incubated with a polyclonal rabbit-antitubulin antiserum (kind gift of Dr. Frank Solomon) diluted 1:10000 in PBS. This was followed by an incubation with a fluorescein-conjugated goat-anti-rabbit IgG antiserum (Cappel, No. 1612–0081) diluted 1:100 in PBS. The cells were then postfixed in 95% ethanol/5% acetic acid for 5 seconds and rinsed three times in PBS. This was followed by an incubation with undiluted hybridoma supernatant from the monoclonal mouse-anti-nestin anti-body (Rat 401). Finally, the cells were incubated with a rhodamine-conjugated polyclonal goat-anti-mouse IgG antibody (1:100 dilution, Cappel No. 2611–0231). After two brief rinses in water, the cells were covered with Immumount (Shandon) and inverted onto clean glass microscope slides. As control experiments for potential cross-hybridization and spillover between the fluorescein and rhodamine spectra in the fluorescence microscope, the first antibodies (rabbit-anti-tubulin and mouse-anti-nestin) were omitted in two separate experiments under otherwise identical conditions. No cross-hybridization or significant spillover was observed. In the colchicine experiments the St15A cells were grown as above and treated with colchicine at 25 ug/ml for 24 hours followed by fixation and staining as described here.

In the actin/nestin double-label experiments ST15A cells were grown as above and fixed in 4% paraformaldehyde, 0.1% Triton X-100 in PBS for 5 minutes. After blocking as described above, the cells were incubated with 0.16 uM rhodamine-conjugated phalloidin, as suggested by the manufacturer (Molecular Probes). Rinses, postfixation and staining with the nestin monoclonal antibody were performed as described above, with the exception that a fluorescein-conjugated sheep-antimouse IgG second antibody (diluted 1:00, Cappel No. 1606–3152) was used. No cross-hybridization or spillover was observed after omitting the rhodamin-conjugated phalloidin or the nestin antibody. In the cytochalasin B experiments the ST15A cells were treated with cytochalasin B at a final concentration of 10 ug/ml for 60 minutes, otherwise all immunostaining procedures were identical.

In the vimentin/nestin double-label experiments ST15A cells were fixed in 4% paraformaldehyde, 0.1% Triton X-100 in PBS for 5 minutes. After blocking, the cells were incubated with a polyclonal goat-anti-vimentin antiserum (dilution 1:20, MILES 65–794) followed by a fluorescein-conjugated rabbit-anti-goat IgG second antibody (dilution 1:100, ICN 65–176). Incubation times and rinsing procedures were as described above. Postfixation and incubation with the anti-nestin antibody were performed as in the tubulin/nestin experiments. No cross-hybridization or spillover was detected after omitting the anti-vimentin and anti-nestin antibodies, respectively. In all experiments the mounted cells were photographed on Kodak Ectachrome 400 ASA using a 63X objective on a Zeiss fluorescence microscope.

EXAMPLE 2 Production of the Rat 401 Monoclonal Antibody

Developing monoclonal antibodies were generated to fixed spinal cord from embryonic day 15 (E15) rats. Timed pregnant female rats were obtained from Taconic Animal Supply Co. and housed until the appropriate gestation age. Uteri were dissected from pregnant animals into ice-cold phosphate buffer (pH 7.4), individual enbryos were removed and the spinal cord was dissected free of other tissue into fixative (4% paraformaldehyde in 0.1 M phosphate buffer).

The immunization and fusion protocol has been described previously (McKay and Hockfield, Proc. Natl. Acad. Sci. USA 79: 6747–6751 (1982)). Briefly, BALB/c mice received two intraperitoneal immunizations with fixed tissue homogenized in saline and suspended in an equal volume of Freud's complete adjuvant and a final intravenous boost of unfixed tissue with adjuvantSpleen cells from immunized mice were fused with NS1 myeloma cells and resulting hybrid cell lines were screened immunohistochemically on 100 μm-thick Vibratome sections of 4% paraformaldehyde-fixed E15 rats. Lines producing antibodies of interest were cloned in soft agar or by limiting dilution and antibody subclass was determined by the Ouchteriony method (Ouchteriony and Nilsson, Immunodiffusion and Immunoelectrophoresis. In *Handbook of Experimental Immunology* D. M. Weir, ed., Blackwell Scientific Publications, Oxford (1978).

Immunohistochemistry

Tissue for immunohistochemistry was fixed either by intravascular perfusion or by immersion. All postnatal material was fixed by intravascular perfusion (under ether anesthesia) with 4% paraformaldehyde at pH 7.4 for light microscopy or with either 4% paraformaldehyde at pH 10.0 or 4% paraformaldehyde, 0.1% glutaraldehyde at pH 7.4 for electron microscopy. The CNS was dissected out and stored in 0.1 m phosphate buffer (pH 7.4) with 0.1% sodium azide. For prenatal material, pregnant females were ether anesthetized, uteri were dissected into cold 0.1 m phosphate buffer and the females were killed by cervical dislocation. Embryos were dissected individually into Sylgard-coated Petri dishes and pinned in place. Intravascular perfusion was performed by opening the skin of the thoracic cavity, nicking the right atrium with a fine forceps and placing a 25 gauge needle into the left ventricle. One to 5 ml of fixative (as above) were injected into the heart. The embryos were placed in a vial containing the same fixative for 4 hr and then stored in phosphate buffer. E12 to term embryos were fixed by perfusion (using a 30 gauge needle for E12 embryos); E10 and E11 embryos were fixed by immersion in fixative. E13 and older animals were sectioned at 50 to 100 μm on a Vibratome without additional support. E10 to E12 embryos were embedded in 15% gelatin before sectioning Immunohistochemical reactions were performed on free-floating sections by sequential incubations in monoclonal antibody as full-strength supernatant (12 to 20 hr); horseradish peroxidase (HRP)-conjugated goat anti-mouse antibody at a dilution of 1:100 in tissue culture medium with 10% serum; and 3.3′-diaminobenzidine (DAB; 0.025%) with $H_2O_2$ (0.002%). Peroxidase-conjugated lectins (Sigma Chemical Co.) were used at serial dilutions in the same manner with the omission of the peroxidase-conjugated goat anti-mouse antibody. For light microscopy, 2% Triton X-100 was included in both antibody solutions. For electron microscopy sections carried through this procedure (without Triton X-100) were post-fixed in 2% $O_2O_4$ embedded in Epon-/Araldite between plastic coverslips, and cut at 1 μm and 0.12 μm for correlative light and electron microscopy. For high resolution light microscopy, sections (Triton-treated) were embedded in plastic as for electron microscopy and sectioned at 2 μm.

Immunoblots

The apparent molecular weights of antigens recognized by antibodies were determined using the method of Towbin et al., *Proc. Natl. Acad. Sci. USA* 76: 4350–4354 (1979)). Proteins were extracted from unfixed tissue with sodium dodecyl sulfate (SDS) and β-mercaptoethanol and run on an SDS-polyacrylamide gel. The proteins were electroblotted onto nitrocellulose paper which was then exposed to primary (1 hr) and secondary (1 hr) anti-bodies. HRP was visualized with 4-chloronaphthol.

EXAMPLE 3 Chacterization of Rat Nestin from the ST15A Cell Line

ST15A cells were derived from rat postnatal day 2 cerebellum after infection of a primary culture with a retrovirus transducing the temperature sensitive, tsA58 allele of SV40 T antigen (Frederiksen et al., 1988)). ST15A cells were plated on tissue culture plastic coated with polyornithine and passaged at the permissive temperature, 33° C., in Dulbecco's modified Eagle's medium (DME) supplemented with 2 mM L-glutamine, 1 mM sodium pyruvate and 15 mM HEPES, pH 7.2, containing 10% fetal calf serum (FCS). For the experiment in FIG. 8, confluent cells (labelled 'day 0') were transferred into DME/10% horse serum (HS) and cultured at 33° C. or 39° C. as marked for the indicated time. 39° C. is the non-permissive temperature for tsA58.

Primary cultures were prepared from P4 rat cerebellum as previously described (McKay, R. D. G. et al., Cold Spring Harbor Symp. Quant. Biol. (1990). Briefly, tissue was dissociated by trypsinization followed by trituration. Cells were plated on polyornithine-coated coverslips in DME/10% FCS/10% HS and grown at 39° C. for 24 hours. The medium was changed to DME/10% HS and culture continued for 6 days.

The medulloblastoma cell line was derived by growing cells from dispersed, fresh medulloblastoma tissue. The tissue was removed from a previously untreated tumor in a 10 year old female. The cell line has not been cloned. Cells were passaged in Ham's F12 supplemented with 20 mm L-glutamine and 10% FCS.

Immunocytochemistry

Cells for immunocytochemistry were fixed in 4% paraformaldehyde buffered with 50 mM sodium phosphate, pH 7.2, for troponin staining or buffered with 50 mM sodium borate, pH 9.5, for nestin staining. The antibodies used were mouse monoclonal Rat 401 (Hockfield and McKay, supra (1985), mouse monoclonal antibody against troponin T (Sigma T-6277), and rabbit polyclonal serum raised against the C-terminal region of nestin expressed in bacteria. Fixed cells were incubated in primary antibody for one hour, rinsed 3 times in PBS, incubated for one hour with flourescein-conjugated goat anti-rabbit serum (Organon-Tetnika) and mounted in Immumount (Shandon, Inc.) with 2% DABCO. Medulloblastoma tissue and normal human cerebellum were frozen and subsequently fixed in formalin. 50 um sections were cut and stained with rabbit polyclonal serum raised against the C-terminal region of nestin.

Isolation of RNA and Northern blotting

Cultured cells were scraped into 5M guanidine thiocyanate/25 mM citrate, pH 6.8/ 0.5% N-lauryl sarcosine/0.1 β-mercaptoethanol and RNA pelleted through a CsCl step gradient (Chirgwin et al., 1979). 20 ug of total RNA was electrophoresed through a 1% agarose/2.2M formaldehyde gel and transferred to nitrocellulose. Prehybridization and hybridization were in 50% formamide/5xSSC/5X Denhardt's/0.1% SDS/0.1 mg/ml salmon sperm DNA at 42° C. Filters were washed in 2xSSC/0.1% SDS at room temperature and in 0.1xSSC/0.1% SDS at 55° C. and exposed to X-ray film with an intensifying screen. Filters were stripped by washing 6 times for 3 minutes each in boiling 0.05xSSC/0.1% SDS/20 mM EDTA, pH8, and rehybridized. Probes were prepared for hybridization by random priming on fragments isolated on low melting temperature agarose gels (Feinberg and Vogelstein, supra (1984). The following plasmids were used to generate probes: mouse myoD1 cDNA pEMC11s (Davis, R. L. et al., Cell. 51: 987–1000 (1987); mouse myogenin cDNA p65 (Wright et al., supra (1989); rat nestin cDNA p401-16; human B-actin cDNA (Gunning, P. et al., Mol. Cell. Biol. 3: 787–795 (1983)).

Western Blotting

Proteins were extracted from cultured cells or rat postnatal day 5 limb muscle (Sprague-Dawley; Taconic, Inc.) in the presence of aprotinin and PMSF in 2% SDS, 5 mM EDTA and 15% glycerol in 0.1M Tris, pH 6.8. 50 ug of total protein was run in each lane of an SDS reducing gel according to Laemmli (Laemmli 1970); proteins were transferred to Immobilon P membranes (Millipore) using a Hoeffer transfer apparatus at 50 volts for 4 hours. Filters were blocked in 5% BLOTTO (Johnson, D. A. et al., Gene Anal. Tech. 1: 3–8 (1984)) overnight. Rat 401 hybridoma supernatant was used undiluted; troponin T antibody was diluted 1:500; polyclonal anti-nestin antiserum was diluted 1:1000; HRP conjugated secondary antibodies were purchased from BioRad.

EXAMPLE 4 Characterization of Human Nestin

To characterize human nestin, a new antiserum, designated anti-nestin 129, was raised to recombinant rat nestin expressed in E. coli since the rat-401 mAb failed to recognize human nestin in immunohistochemical and immunochemical assays.

Production of Anti-nestin Antiserum

The insert from the clone λgt10 401:16 (Lendahl, U. et al., Cell 60: 585 (1990)) was isolated and ligated into the pATH1 vector (Tzagaloff, A. et al., J. Biol. Chem. 262: 17163 (1986)), producing a clone in which the bacterial TrpE protein (37.2 kD) was fused at its C terminus with the last 1197 amino acids of nestin. The fusion protein was induced in E. coli strain HB101 with 20 μg/ml indoleacrylic acid (Sigma I1625) for 4 hours as described in (Tapscott, S. et al., Science 242: 405 (1988)). The TrpE-nestin fusion protein migrates at greater than 200 kD in 6% SDS PAGE gels, making it the largest protein in the bacterial lysate. The fusion protein was purified by cutting the top band from the gel. Anti-nestin antiserum 129 was produced by injecting the fusion protein subcutaneously into a female NZW rabbit. The characterization of anti-nestin 129 and its specificity for human nestin is described here.

First, this antiserum was compared to the Rat-401 MAb in immunochemical and immunohistochemical studies of postnatal day 6 (P6) rat cerebellum. Then, anti-nestin 129 was used to probe human CNS tissues, tumors and tumor derived cell lines. To determine if nestin co-localized with other IF proteins, double and triple immunofluorescence experiments also were performed using anti-nestin 129 and antibodies to vimentin, glial fibrillary acidic protein (GFAP) and neurofilament (NF) triplet proteins. Finally, Western blots were performed on cytoskeletal extracts of some of the tumor derived cell lines to identify human nestin and to compare it with rat nestin as well as with the class III and IV IF proteins expressed by CNS cells.

Specificity of Anti-Nestin 129 in the Rat

The rabbit anti-nestin antiserum produced as described herein, i.e. anit-nestin 129, yielded results identical to those produced by the Rat-401 MAb when both were used to probe P6 and adult rat CNS tissues by immunoblots and immunohistochemistry. On immunoblots of cytoskeletal extracts from P6 rat cerebellum separated by SDS-PAGE, anti-nestin 129 identified a band with an apparent $M_r$ of 240 kD. This band was identical to the band labeled by Rat-401. Further, both antibodies labeled similar bands in lysates of the induced bacteria producing the TrpE-nestin fusion protein.

In immunohistochemical studies of the P6 rat cerebellum, anti-nestin 129 labelled radial glial cells very intensively. The processes of these cells radiated from the internal granular layer to the external granular layer. These radial glia also were labeled with Rat-401 and the anti-vimentin MAb. Neither of the anti-nestin antibodies stained immature Purkinje cells or other neurons. In contrast to the P6 rat cerebellum, the anti-nestin 129 and Rat-401 antibodies only stained blood vessel endothelial cells in the adult rat cerebellum, while the anti-vimentin MAb (V9) labelled blood vessels, white matter astrocytes and radial glial fibers. Furthermore, nestin immunoreactivity was demonstrated by both anti-nestin antibodies in immature skeletal muscle of the P6 rat as well as in Schwann cells of adult rats (data not shown).

These studies demonstrate that this new anti-nestin antiserum yields immunohistochemical results in the human developing spinal cord, cerebrum and cerebellum that were nearly identical to those produced by Rat-401 and the anti-nestin antiserum in the rat.

EXAMPLE 5 Cloning of the Human Nestin Gene

The human nestin gene (SEQ ID NO: 3) was isolated using low-stringency DNA hybridization of a human genomic bacteriophage lambda library with a rat nestin probe.

A genomic library in the vector EMBL 3 made from partially Sau3A-digested human genomic DNA (Clontech) was screened using a $^{32}$P-labelled probe derived from the rat nestin gene starting at 202 nucleotides upstream of the translation start and ending at nucleotide 483 after the translation start (Lendahl, et al., 1990) under the following conditions: prehybridization in 6X SSC, 5X Denhardt's solution, 0.5% SDS and 100 micrograms/ml salmon sperm DNA at 65° C. for 1 hour; hybridization in the same conditions except for using 50 micrograms/ml salmon sperm DNA and hybridizing for 16 hours. The filters were then washed for 2×30 minutes at 48° C. in 2X SSC and 0.25% SDS.

One positive clone out of $1.5 \times 10^6$ placques screened contained the entire human nestin gene and was chosen for further analysis. This clone was purified and grown in large scale (Maniatis, et al., 1989). A restriction map was established and EcoRI fragments were subcloned in the plasmid vector Bluescript KS I (Stratagene).

EXAMPLE 6 Nestin Expression in Brain Tumor Samples

Immunohistochemical data on the expression of nestin, other IF proteins and synaptophysin (SYP) by a diverse group of 34 CNS tumors are summarized in Table 2.

TABLE 2

| No. | Age (Yr) | Sex | Material | Location | Nestin | Vim | GFAP | NP | SYP |
|---|---|---|---|---|---|---|---|---|---|
| PNETs | | | | | | | | | |
| PNET + N,G | | | | | | | | | |
| 1 | 1 | M | F | posterior fossa | + | +++ | + | + | − |
| 2 | 1 | M | F | posterior fossa | + | +++ | + | +++ | +++ |
| 3 | 5 | F | F | posterior fossa | ++ | + | + | + | ++ |
| 4 | 1 | M | F | posterior fossa | ++ | ++ | + | + | +++ |
| 5 | 1 month | F | F | posterior fossa | ++ | ++ | + | +++ | + |
| 6 | 5 | M | F | posterior fossa | ++ | ++++ | ++ | + | + |
| 7 | 8 months | F | F | posterior fossa | +++ | +++ | ++ | + | + |
| 8 | 1 | F | F + P | posterior fossa[a] | ++ | ++ | + | + | +++ |
| PNET + N | | | | | | | | | |
| 9 | 13 | F | F | posterior fossa[b] | − | ++++ | − | ++ | ++ |
| 10 | 6 | M | F | posterior fossa | − | + | E | ++ | ++ |
| PNET + G | | | | | | | | | |
| 11 | 11 | M | F | posterior fossa | + | +++ | ++ | P | + |
| 12 | 4 | F | F | posterior fossa | +++ | ++++ | ++ | P | +++ |
| PNET, NOS | | | | | | | | | |
| 13 | 2 | M | F | pineal | ++ | ++ | − | − | ++ |
| 14 | 11 | M | F | posterior fossa[b] | − | + | − | − | ++ |
| 15 | 14 | M | F | posterior fossa[b] | + | +++ | − | − | + |
| Astrocytic tumors | | | | | | | | | |
| 16 | 2 | F | F | posterior fossa[c] | ++ | ++++ | ++++ | − | − |
| 17 | 6 | F | F + P | posterior fossa[c] | − | ++++ | +++ | − | |
| 18 | 6 months | M | F | hypothalamus[c] | ++ | +++ | +++ | − | − |
| 19 | 17 | M | F + P | posterior fossa[d] | − | +++ | +++ | − | − |
| 20 | 3 | M | F | frontal[e] | +++ | NA | + | − | NA |
| 21 | 6 | M | F + P | occipital[f] | +++ | +++ | +++ | − | − |
| 22 | 13 | M | F | posterior fossa[f] | +++ | +++ | +++ | − | − |
| Ependymomas | | | | | | | | | |
| 23 | 3 | F | F | parietal | ++ | ++++ | + | − | − |
| 24 | 2 | M | F | posterior fossa | + | − | + | − | − |
| 25 | 3 | M | F + P | posterior fossa | ++ | ++++ | +++ | − | − |
| 26 | 5 | M | F + P | posterior fossa | ++ | ++++ | ++ | − | − |
| 27 | 15 | F | F + P | cerebral hemisphere[g] | ++ | ++++ | + | − | − |
| 28 | 8 | F | F + P | parietal[h] | +++ | +++ | ++ | − | − |
| Choroid plexus papillomas | | | | | | | | | |

TABLE 2-continued

| | | | | | Immunoperoxidase staining of brain tumors | | | | |
|---|---|---|---|---|---|---|---|---|---|
| No. | Age (Yr) | Sex | Material | Location | Nestin | Vim | GFAP | NP | SYP |
| 29 | 1 | M | F | posterior fossa | − | +++ | + | − | − |
| 30 | 2 | M | F | lateral ventricle[i] | − | +++ | − | − | − |
| Gangliogliomas | | | | | | | | | |
| 31 | 2 | F | F | temporal | ++ | +++ | +++ | + | − |
| 32 | 1 | F | F | occipital | ++ | ++ | +++ | + | − |
| Meninglomas | | | | | | | | | |
| 33 | 8 | M | F | posterior fossa | ++ | ++ | − | − | − |
| 34 | 27 | M | F + P | anterior fossa | + | +++ | − | − | − |

Legend to Table 2
Summary of the data obtained from the immunoperoxidase studies of each of the brain tumor samples. Results from frozen (F) and paraffin (P) material are combined in the cases in which both kinds of material were studied. The patterns of staining are described as
− = no staining,
+ = positive in less than 5% of tumor cells,
++ = positive in between 5–50% of tumor cells,
+++ = positive in between 50–95% of tumor cells,
++++ = positive in more than 95% of tumor cells,
E = positive cells equivocal, i.e. reactive astrocytes of tumor cells,
P = interstitial filamentous staining in the neuropil.
The following antibodies were used to obtain these data;
nestin (rabbit anti-nestin antiserum 129),
vimentin (V9),
GFAP (2.2B10),
NF (RMS12, RMd020, RMO254, HO14, DP1, TA51, RMO24).
NA = not available due to limited material;
PNET + N,G = PNET with neuronal and glial differentiation;
PNET + N = PNET with neuronal differentiation;
PNET + G = PNET with glial differentiation;
PNET − NOS = PNET, not otherwise specified.
[a]reccurent tumor of case 7,
[b]autopsy case,
[c]benighn astrocytoma
[d]genighn strocytoma + angioma,
[e]anaplastic astrocytoma
[f]glioblastoma multiforme,
[g]mixed ependymo-astrocytoma,
[h]anaplastic enpendymoma,
[i]choroid plexus carcinoma.

The results from frozen and ethanol-fixed paraffin-embedded samples from the same biopsy are combined in the 10 cases from which these paired samples were available. Notably, the immunohistochemical results obtained from each of these paired samples were identical, although the primary antibodies were used at slightly higher dilutions in the frozen material compared with the paraffin material.

PNETs The anti-nestin antiserum stained tumor cells in 12 of the 15 PNETs examined here. Nestin immunoreactivity was found in the cytoplasm of individual neoplastic cells. Reactivity was also observed in the coarse processes of large stellate cells, as well as in blood vessel endothelial cells. In the PNETs with an insular architecture, nestin reactive cells were found both within and outside the islands. Since PNETs express SYP and other neuroendocrine markers as well as all classes of IF proteins (Gould, V. E. et al., Human Pathol. 21:245 (1990)), the PNETs were probed for SYP. These studies demonstrated SYP in 14 of 15 PNETs. Vimentin was detected in all the PNETs. Ten of the 15 PNETs expressed GFAP and 10 expressed 1 or more NF proteins. Double immunofluorescence studies of nestin and NF proteins, as well as nestin and GFAP on frozen sections showed their co-localization in the same cells (data not shown). The immunohistochemical data on GFAP and NF proteins suggested that 15 PNETs could be classified into 4 subtypes, i.e. 3 cases of PNET-NOS (not otherwise specified), 2 cases of PNET+G (PNET with glial differentiation), 2 cases of PNET+N (PNET with neuronal differentiation) and 8 cases of PNET+G,N (PNET with glial and neuronal differentiation). All 8 cases of PNET+G,N showed nestin immunoreactivity and 2 cases of PNET+G expressed nestin. On the other hand, 2 cases of PNET+N were negative for nestin. These results may indicate that PNETs with neuronal differentiation tend to lack nestin expression in contrast to PNETs with glial differentiation. This phenomenon paralleled normal differentiation in that postmitotic neuroblasts did not express nestin whereas radial glial cells did, even at relatively late developmental stages. Two of 3 cases of PNET-NOS showed nestin positive tumor cells. This immunohistochemical phenotype might represent primitive neuroepithelial cells or immature radial glial cells in the developing CNS. The other PNET-NOS case was negative for nestin and it might correspond to extremely immature CNS precursor cells just like the most undifferentiated PNET cell line (i.e. Daoy).

Astrocytic tumors Five of 7 astrocytic tumors displayed positivity for nestin in the perinuclear cytoplasm of the tumor cells as well as in the cytoplasmic processes of these cells. Additionally blood vessel walls were nestin positive. Two of 4 benign astrocytomas were negative for nestin. One anaplastic astrocytoma and 2 glioblastomas showed strong nestin positivity. In the glioblastomas, multinuclear giant cells were stained strongly.

Ependymomas Six tumors were histologically diagnosed as ependymomas and all showed nestin positivity. Immunoreactivity for nestin was found in the tumor cells which formed perivascular pseudo-rosetts. One ependymoma (with marked nuclear pleomorphism, necrosis and a few mitoses) was diagnosed as an anaplastic ependymoma and it demonstrated the strongest nestin immunoreactivity among the 6 ependymomas. Expression of nestin described here indicates that nestin is the dominant IF protein of early CNS precursor cells. However, nestin is rapidly extinguished in neurons, glia and other CNS cell types derived from these precursors. The mechanisms responsible for these rapid changes in IF protein expression are unknown.

In contrast to the restricted expression of nestin in normal developing CNS cells, this IF protein was ubiquitously present in a wide variety of CNS neoplasms. Nestin was expressed in a subset of PNETs, but was more abundant in gliomas. The presence of nestin in diverse types of neuroepithelial tumors is similar to vimentin, but distinct from the distribution of GFAP and NF proteins in CNS tumors.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

We claim:

1. Isolated DNA encoding nestin protein and consisting of the nucleotide sequence of SEQ ID NO: 1.

2. Isolated DNA encoding nestin protein and consisting of the nucleotide sequence of SEQ ID NO: 3.

3. Isolated DNA encoding nestin protein consisting of a nucleotide sequence which hybridizes to the DNA sequence of SEQ ID NO: 3 under high stringency conditions.

4. Isolated DNA which encodes a protein of mammalian origin whose expression distinguishes neural multipotential stem cells from neuronal, glial and muscle cells wherein the amino acid sequence of the encoded protein is SEQ ID NO: 2.

5. Isolated DNA which encodes a protein of mammalian origin whose expression distinguishes neural multipotential stem cells from neuronal, glial and muscle cells wherein the amino acid sequence of the encoded protein is SEQ ID NO: 4.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 11236 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:1:

```
CGTGTTTGCT TTAGCAAGAC GTCTTTTTAC CTGTGTACCC CAAAAAACAT CATTTGATGT    60
AACTAACTTA CTCAAGGCTA TTGAGCCAGA GGGGAAATTC AGAGCCACCA GTGCAAGGCA   120
CAGTGCCATA AGGGTCATAG TCAAGCACTT GCAGTCTCTT TAGAACATGG TCGGTGCTCA   180
GAGAAGGATA GAGAAAAGGA AAGATACCCT CTTTGCCCGG AGACCTCCGG CGGGAAAATT   240
TATATGATCC ACAGTAGTGG GTATGTAACA GGCATACAAG CCAAACACTG ATAGTCATAA   300
AGACATTCAT GTTAGAACAA ATTCTTGGTA TACAGATTAT TTTTCCATTT TTAAAAGATG   360
AAAGAAGCTT TTCCTGCTAA TGGGAAGGAT CGCTTGTTTA TCCTCACGTA GCATTGAATG   420
TTCTTGGCTG AACATTTGGT ATTTAAAACC ATGGTAGAAC ATCTTCAACG TTTTCAGAAT   480
TGATCCATAC TTTGATTTAA AAAGTAGTTT ATTGGGTTGG GATTTAGCTC AGTGGTAGAG   540
GCTTGCCTGA AGCCAAGGCC TGGTTCGTCC CACGACGTCT CGCAGAAAAA AGAGAAAGA   600
AAAAGTAGTT TATTGCTATT TCTGTGTGTG TGTGTGTGTG TGTGTGTGTG TGTGTGTGTG   660
TGTGTCTGTG TATGTCTGTG CATGGGCAGT ATACCTGTGT GTGGATGCAC ATAGAGGTCA   720
GAGGCCTTTG ATGTCCCTGG AGCTGATATG GGTGCTGAGA ATTGTACTTG GGTCTCCGGG   780
AGAGCAGCAA GTGCTTTTGA CGACTTAGCA TCTCTCCAGC TCAGATATCC TGATTTTCTA   840
ACTGTCAATG CTGGGAATGC CAATCTGTAT GAATGATTCT GCCCACAGCA GAAGTATGTT   900
TAGGACCATT TCAGAAATTG TTGGAAATTT TGTCCTAATC GTAAGCCAAA ATTCACTGAA   960
GGATTTTATT TTTCGTTTGA GACAGGATCT TACTATGTAA TCCTGGCTGG CCTGGAACTC  1020
ATTTGCTATG TAGAGGCTGG CCTTAAACTC AGAGATTGGC ATTATTCTGT CTCTTGAGTG  1080
CTGGGATTAA AGGAATTAAA CTGGCCTCAC TGAACGAGGT TTGATGACAC TCAAGTTATC  1140
GACTCAAACA GCTATTTAAA AGAATTTAGA TTTATTACTG TTGTTATTGT TGTTAGTCTG  1200
TGTGTGTGTG TGTGCGCGCG AGCGCAGGTG CACCATGCTA CAGTATGCCA TGTGCGAGTC  1260
AGTTCTCTCC TCACTATGTG GGTCCTGAAC ATCATGGGAG GGAGCTTGGC AACAGGCACT  1320
ACCGGCACTG AGCAGCGACT CAGAGCTCAC ATCTCAATCC ACTAGCACAA GGCAGAGAAG  1380
GAGCTACTGC AACCTCTCTC AAAGCCTACC CCCAGTGATA CACCTCCTCC AACAAGGCCA  1440
TTCCTCCCAA TCCTTCTAAA ATAGGTTCTC CAACTGGGGA CCAAGCATTC AAACATTTAA  1500
```

```
GCCTAAGGGT CCCTTGTACA AAGTCCACAA CTTCATTTCT TTCTTCGCCA GACTGCATCG    1560
TTAGCCACCA GGGGGCTCCC CTGAGAGCCG CGTAGCTTTC TAACTGAGTA AACTGCAAGA    1620
GTGTACGAAC AACAAGGAG AAAAACTTTC TTGAACGTAT GACGTCCCTT GCCATTTTCC    1680
TTTTCCTGAT GCGGGATGAG GAGGGGGAGG ACGTCCCTCT GCGGGTACGA ACTGTGCATT    1740
GTGTCTGTTA ACATCAACTG GGCTGGCTGG GCAGGGGTGT TGGCACAGAC CTTTAATCCC    1800
AGCACTAGGG AGGCTAAAGC AGGAGCATCT CTACGATTTC GAGACCAGCC TGATTCACAT    1860
AGCGATACCA ACCATCTGAA GAAAGGGGTG GGGGTGTTT ACTGCCCAGG CTGGCCTTAA    1920
TCCTTCTTCG GGCTTCGGAG CTCAGGAAAA CCCAGTACCA GTGGGTTTTT CTTGCTTCGG    1980
GCAGTGTCTC TCTGCAATGT TGCCTCCCTG GACAGGTGG TGGTGGTGGT GGTGGTGGTG    2040
GTGGTGGTGG TGGTGGTGG GGTGGTGGTG GTGGTGTGTG AATATTTACT GTTTTACACA    2100
AAACACTGCA CCGTCCGTTT TTCCAACAGT TCATGAGGAT CCAACACCA AGCCATTCTA    2160
TAAATAAGAA GCCGAGTCTC AGAGAATTTG AGTGTGTAGA GAAAGGAGGT CCGCAGGCCC    2220
AGTTCTGTGC ATCATAGGGT GTTCCGGGGT GTCTGGCTGT ATCTCAAGAT TCTCTCAGAA    2280
AATCACCCGC ACCGGACCGG ATCCCTCAGG GAGGGGCTGC ACTTTGGTTC TTCTCTTCTG    2340
CACCCGGATG AAGCAGGAAC CCCGGTTGCG TGTTGCACTG AACGCTAAAG GGTTAAGGCC    2400
TGGGGGGCCG CCCCTTTTCC GCCCAGCCGG CGGGAGTATG AATACCCTCG CTCCAGCTCC    2460
CTGCTGGAGT TCTCCGCTTC CGCTGGGTCA CTGTCGCCGC TACTTCTTTT CAACCCCTAA    2520
AAGCTCCACG GGCCACTCCC TTCTCTAGTG CTCCACGTCC GCTTGCCCTC GGGGCCAGA    2580
CCAGCGACAT GGAGGGTTGC GTCGGGGAAG AATCTTTTCA GATGTGGGAG CTCAATCGAC    2640
GCCTGGAGGC CTACCTGACC CGGGTCAAGA CGCTAGAAGA GCAAAACCAG CTGCTCAGCG    2700
CCGAGCTTGG GGGACTCCGG GCGCAGTCCG GAGACACCTC CTGGAGAGCC CGAGCCGATG    2760
ACGAGCTGGC ATCCCTGCGG ATCCTCGTCG ATCAGCGCTG GCGGGAGAAG CTCGAGGCTG    2820
AGGTGCAGCG CGACAACCTT GCGGAAGAGC TGGAGAGCGT GGCGGGCCGG TGCCAGCAGG    2880
TGCGGCTTGC TCGGGAGCGG ACCGTCCAGG AGGCCGCCTG CAGCCGGCGC GCACTCGAGG    2940
CGGAGAAGAA TGCGCGGGGC TGGCTGAGCA CCCAGGCGGC CGAGCTGGAG CGGGAGTTAG    3000
AGGCTCTGCG AGCCGCGCAC GAGGAGGAGC GCGCACACCT GAACGCCCAG GCCGCCTGTG    3060
CGCCTCGCCG GCCCCCCGCA CCGCCCCACG GATCCCCGGT CCGGGCCCCC GAAGTCGAGG    3120
ATCTGGCCAG GCGACTAGGC GAAGTGTGGC GCGGGGCGGT GCGTGACTAC CAGGAGCGCG    3180
TGGCTCACAT GGAAAGCTCG CTGGGTCAGG CACGCGAGCG GCTGAGCCAA GCCGTGCGGG    3240
GCGCTCGGGA GTGTCGCTTA GAGGTGCAAC AGCTGCAGGC TGATCGCGAC AGCCTCCAGG    3300
AGCGCAGAGA AGCGCTGGAA CAGAGATTGG AAGGCCGCTG GCAGGACCGG CTGCAGGCCA    3360
CTGATAAGTT CCAGGTGAGG AGGGTCACCA ACTTCCTCCC CGACTACCCG CCCCCACACA    3420
GACCCGTAAG ACCAAGCCCT AGGAAGTACT TAGGATGGCA AGAGACCTTC AGGAAGGGGC    3480
TGGAGGAAAG GGCGACTGTA TTCATGAGTC CTGCCCAGAG CAAGCACAGG CCCTAAACTT    3540
TCCTGTCCAA GCAGGATGGG CGGATGGAAT TCTGAGACCT CCTTAGCAGA GCCCGCTTAA    3600
AGGACGACAG GCCAATTCCC ACTGTAGCAG CTCCTCACTC TTTGAAGGGC AATTTCACTC    3660
TAGGATGATT CCCTGCGCCC TTCCCTTTGC TGTTGTCAAT CAGAAGGTGC CCAGCACATG    3720
CTCCCTCAGC ACCAGAAGGT CCCTAGCAAC CATAGTGAAG GAAGGCGGGG TGAGCCACCG    3780
CCGACCACCA GCCCCTCTCT GTGTCAAGGC TTCTCAGCTC CCTGAAGCAC ATTCCAAAGG    3840
CCTGGGGCAC CCTCCCCCTT ATACTGCACA GATGTAACCA ACAGCTGAGA AAACAGCTCT    3900
TGCCTGGCCC AGACAGAAGC CCCGACACGG CCATCTGCCC ACTCTTCTTG GGGGAGAAAG    3960
```

-continued

| | | | | | |
|---|---|---|---|---|---|
| ATTCCAGAAC | ACGTGGGAAG | TGGAGGAACC | CAGCCTGCTA | TGAGGAGCTG | GGGACAGTGA | 4020 |
| TGGCCAACGG | ATTTCCTTCC | ACGTCCTCCC | AAGCCGACTC | TTGATAAATT | GCTTTTCCCT | 4080 |
| TCTGTTTCCA | TTTTACCTCC | TCTTCTGCTG | TGTAACCCAT | CCCCGTGGGA | GCTAGATTCT | 4140 |
| CAATAGCATG | TGTTACCATT | TAATGAGCAT | CCTCAAGAGA | AGCCTGGTCT | AGGAGAGGCA | 4200 |
| TGGAGTGTTC | CCTGAGCTTG | TCTGTGGGTT | CCAGTGCAGG | GAGGACATAG | AACAGGAGTC | 4260 |
| CTACAGAGAA | GTGAGCAGTA | AGGAGCCTCA | GGGCCAGAGC | GGAGGCTCCT | TCCACTCACT | 4320 |
| CTTCCCGCTT | GCCTTGCAGC | TGGCTGTGGA | AGCCCTGGAG | CAGGAGAAGC | AAGGTCTACA | 4380 |
| GAGTCAGATC | GCTCAGATCC | TGGAAGGTGG | GCAGCAACTG | GCACACCTCA | AGATGTCCCT | 4440 |
| TAGTCTGGAG | GTGGCTACAT | ACAGGTACAC | AGTGCTGACT | GTCCTCGGCT | TCTTCTGCGG | 4500 |
| CCCAGAAACT | TGGCTTTGTA | CTTTCTGTGA | CTGTCAGCTA | TCGCTTTGTA | AAACTGTCCT | 4560 |
| ATTTATGTGT | ATTTGTGTAT | GTACCACATG | TGTACAGGTG | TCCTAAGAGC | CCAGAGGAAG | 4620 |
| GCAATGGGTT | GTGTGCAGCT | CCACACTGGT | GCTGTGAACC | AAACCCTGT | TCTCAGCAAA | 4680 |
| AAGCAGCAAG | CATTCTTAAC | CACTGAGCCG | TCTGTCCAGC | CCTCGGAGTC | ACTTAAAACG | 4740 |
| TTTTATAACA | TTTACTTATG | TAATGTATTT | GTCTGGGATG | GAGGCTTATG | AGTCCCAGAG | 4800 |
| GTGGAACAGG | TCTGGCTTGG | CAGCTTGGCC | CACCCAGGCC | CAGGACCAGA | AGAGAGCGGT | 4860 |
| GATGCTTAAA | AAGACAGCTC | AGTCTTCAGG | GAGGAGACCA | GACAGATGAG | TTCTTTGGAA | 4920 |
| GGCAGGCAAT | CTCCAGTGTC | TATGCCAACA | TCCTGGGGAC | ACCTGGGCAG | TCTCAGAAGA | 4980 |
| GAGGCCTTGC | AGGTTTGCCT | GATCATGCTA | ACCTGCCACC | TCGCCTGGGC | CTCAGGTGTT | 5040 |
| TTGGGTAAGA | GCTGGCCTCC | TAGCTTTTTT | GCTTCCTTTC | AAGCCCTCAT | GTCACTGGTC | 5100 |
| CTGCCCCAGT | TCTCTGCCCT | TTTCTTGGCT | GCCTCAGGAC | GGCTGAGTGG | AACGGCTCTG | 5160 |
| GTGGTATGTT | CACAGCCTCT | GTCTGTGTCT | CTTGTGGGAA | AAGGCCCCAG | TTGGAGTCCC | 5220 |
| ACGGTTGAGG | GCTGAGGATA | TCACTCCAGG | TATGGGCTAG | GACAGGATGC | CCCCCTTTTC | 5280 |
| CAGAATCCAG | CGGTAAAGAG | GAAAGACAGA | GACAGGTCTA | GGAGAGGAGC | TGGAGGGCCC | 5340 |
| AGAGAAGGAC | AGCCAGTGAG | TGTCTAGGAA | AGACTGAATG | CATAAGGCAG | GATGCCGCAT | 5400 |
| GAGGACAGAG | GAAAGGCTAC | TTTGAGAACC | AGATGTGCTC | AGAGGCCATG | AATGGAAACA | 5460 |
| GACTAGTTCC | GAATCCCATG | TGAACTGATT | TCCCTCATCT | CCTTCAATCA | GCTCCATAGG | 5520 |
| CCACTGAGGC | AGGGCCATGA | ACGTTAAGAC | CTCTGCCCTG | AAGAGTTTGT | GATCCTGAGA | 5580 |
| TGAGGGCTTT | AGCCCCAGTC | AGTCCTCTGA | GGGGAAGGGT | CCAGGCAGCT | CTGAGGAATG | 5640 |
| TAACCACTGG | CGTTTGAGGT | CTGAAAAGGA | TTTGGAGAAG | GGAGCTGAA | TTCATTTGCT | 5700 |
| TTTGTCTGTT | ACCAGCTCTG | GGGGCAGAGA | GAGAGCCATC | CCTGGGAAC | AGCCTGAGAA | 5760 |
| TTCCCACTTC | CCCTGAGGAG | CCCTCCCTTC | TTAGGCCCTC | CAGATGGTAG | TGTGGACAAA | 5820 |
| AGGCAATAAT | TAGCATGAGA | ATCGGCCTCC | CTCCCAGAGG | ATGAGGTCAT | CGGCCTTGGC | 5880 |
| CTTGGGTGGG | GAGGCGGAGA | CTGATCTGAG | GAGTCTGATA | TAAGTGTTAG | CAATTCATTT | 5940 |
| GGCCCTGCCT | CCGACTGTGG | GAATCTGCAT | GTGGGGTCTC | CCTGTGTCTC | AAATATGGGT | 6000 |
| TGGCTAAGTA | TATATCTGTG | TGGCTTTTAT | ATGACAATGG | TCACAATAGA | GATTGATCCT | 6060 |
| GCAGTGGCAG | GACATGCTAC | CTCAGCTGGA | GCTGACCCTA | TCTCCCACT | CCCCACCAGG | 6120 |
| ACTCTGCTGG | AGGCTGAGAA | CTCTCGGTTG | CAGACACCTG | GACGAGGTTC | CCAGGCTTCT | 6180 |
| CTTGGCTTTC | TGGGTAAGAG | GCGGAGCCTA | ACTGCTCTCC | TTGGAAGATC | TTCCCTAAGC | 6240 |
| AGCATCAGTC | TAAGCCTTCA | TTCCCTGGTC | CCAACCCTAC | TGATGTTCTC | AGTCTAGCCA | 6300 |
| GTGGGGGTCA | GACAAAATGA | CCAATGTGAG | AACTGCTCTG | GGCTGAGGTC | AGGACATACT | 6360 |
| TACAGTGTTT | CTTACTCTGC | TTTTCCAGAC | CCCAAGCTGA | AGCCGAATTT | CCTTGGGATA | 6420 |

```
CCAGAGGACC AGTACCTGGG ATCTGTGCTC CCTGCCCTCA GCCCCACATC CTTCCCTTCC    6480
CCCTTGCCTA ATACCCTTGA GACTCCTGTG ACAGCCTTCC TGAAGACTCA GGAGTTCCTT    6540
CAGGCCAGAA CCCCCACCTT GGCCAGCACT CCCATCCCAC CTATATCTGA GGCTCCCTGT    6600
CCTCCAAATG CAGAGGTGAG AGCCCAGGAG GTCCCTCTTT CTCTGCTCCA GACACAGGCT    6660
CCAGAGCCCC TTTGGCTGAA GGCCACAGTG CCTAGTTCTT CTGCTATCCT CCCAGAACTA    6720
GAGGAACCTG GGGGCAAGCA GCAGGGTCAC TTCCCTGATG ATCTGACCTC CTTAGCCACA    6780
AACCTCAACC CTCACCACCC TACTTTAGAG GCTAAGATG GAGAATCCAG TGAGTCTAGA    6840
GTTTCTAGCA TATTCCAGGA AGATGAGGGG CAAATCTGGG AACTGGTAGA GAAAGAAGCA    6900
GATATAGAGG TAAAAGTAGA AAACAGCTCA GCCCAGAAAA CACAAGAAAG TGGTCTGGAC    6960
ACAGAAGAAA CCCAGGATTC CAGGGACCT TTGCAGAAGG AAACACTGAA GGCTCTAGGA    7020
GAGGAGCCAC TGATGTCTCT GAAAATCCAG AACTATGAGA CAGCAGGGAA AGAGAATTGC    7080
AATTCTTCTA CAGAAGGCCA CCTGGGAACA CTAGAAGGCC CAGAAAAAGA AAAGCAAATA    7140
CCACTAAAGT CTTTAGAAGA AAAGAATGTA GAGTCAGAGA AAACTCTAGA AAATGGGGTT    7200
CCTGTACTAT CTGAGCTTTT AGGAAAAGAA GACACAAGAA CAGAGGATCA AGAATTAATG    7260
TCTCCTAAAG GTACACTAAA GAGATTTTCA TCTCTAGGAA AGGAAAGTCA AGAAGTAGTG    7320
AGGCCTTCAA AAGAGGGGAA CCTAGAATCA TGGACAGCTT TTAAAGAGGA GAGCCAACAC    7380
CCACTGGGAT TTCCAGGAGC TGAGGACCAG ATGCTTGAGA GACTGGTAGA GAAAGAGGAT    7440
CAGAGCTTCC CAAGGTCTCC AGAGGAAGAG GACCAGGAGG CATGTAGACC TCTGCAGAAA    7500
GAGAATCAGG AACCACTAGG GTATGAAGAA GCAGAGGGCC AGATACTTGA GAGACTGATA    7560
GAAAAGAGA GTCAGGAGTC CCTGAGGTCT CCAGAAGAAG AGGACCAGGA GGCAGGTAGA    7620
TCTCTGCAGA AAGAGAATCA GGAGCCACTA GGGTATGAAG AAGCAGAGGA CCAGATGCTT    7680
GAGAGACTGA TAGAAAAAGA GAGTCAGGAG TCCCTGAAGT CTCCAGAAGA AAACCAGAGG    7740
ATTGGGAAGC CTCTAGAAAG AGAGAATCAG AAATCTCTGA GGTATCTTGA AGAAAACCAG    7800
GAGACTTTTG TACCACTAGA AAGCAGGAAC CAGAGGCCAC TGAGATCTCT AGAAGTAGAA    7860
GAGGAGGAGC AGAGAATTGT GAAACCTCTA GAAAAGTGA GTCAGGATTC CCTCGGATCT    7920
CTAGCAGAAG AGAATGTGCA GCCACTGAGG TATCTGGAAG AAGATGACTG CATAAATAAG    7980
AGCCTTCTAG AAGACAAGAC TCACAAGTCC TTGGGGTCTC TTGAAGATAG AAATGGGGAT    8040
AGCATTATTA TACCACAAGA AAGTGAGACC CAGGTTTCAT TGAGGCCTCC AGAAGAGGAG    8100
GACCAGAGGA TTGTGAACCA TCTAGAAAAA GAAAGTCAGG AGTTCTCGAG GTCTTCAGAA    8160
GAAGAAGAGC AGGTGATGGA GAGATCTCTA GAAGGAGAGA ACCATGAATC ACTGAGTTCT    8220
GTAGAAAAAG AGGACCAGAT GGTTGAGAGC CAACTAGAGA AAGAGAGTCA GGACTCAGGG    8280
AAGTCTCTTG AAGATGAGAG CCAGGAGACC TTTGGACCTC TGGAAAAAGA GAATGCAGAG    8340
TCCCTGAGAT CTCTAGCAGG ACAGGACCAA GAGGAACAGA AGCTTGAACA AGAGACCCAA    8400
CAAACACTGA GGGCTGTAGG GAATGAGCAG ATGGCAGTGA GCCCACCAGA AAAGGTGGAT    8460
CCAGAGTTAC CGAAGCCTCT TGGAAATGAC CAGGAAATAG CTAGATCTCT TGGAAAGAG    8520
AATCAAGAGT CACTAGTGTC ACTGAAAGAA AAAGGTATAG AGACAGTGAA GTCTTTAGAA    8580
ACAGAGATCA TAGAACCACT GGAGACTGCA GAAGAGGACC TGGAAGAAG GAAGTCTATA    8640
GATACTCAGG AGCCATTGTG GTCTACTGAA GTGGCTAGAG AGACAGTAGA ACCTCCAGAA    8700
GATGAGCCCC CAGGATCGCT AGGGTCTGTG GATGAGAACC GAGAGACACT GACATCCCTT    8760
GAAAAGGAGA GTCAAGAACT GAGCTCTCTG GGCAAGTGGA ACGTAGAGAC CAGGGTAGAG    8820
GACAGTCAGC AGTGCCTGCA AGTAGAAGAG GGTCTGCAGG AGGAACAGCA CCAAGAGTCT    8880
```

| | | | | | | |
|---|---|---|---|---|---|---|
| CTGAGAGAGG | TGAAGCAGGA | GCTGCCTAGC | TCTGGAAATC | AACAGCGGTG | GGAGGATGTG | 8940 |
| GTGGAGGGCA | AAGCAGTGGG | TCAGGAAGCA | CCTCTGGCAA | CCACAGGAGT | GGGAACTGAG | 9000 |
| GATAAGGCAG | AGTTGCATCT | GAGGGGGCAA | GGTGGAGAGG | AAGAAGCTGC | AGCAGAGGGA | 9060 |
| GAGCTGTTGC | AGGATATTGT | GGGGGAGGCC | TGGAGTCTGG | GGAGCTCTGA | GCCCAAGGAG | 9120 |
| CAGAGGGTCC | CTGCTGAGGC | CCTCGACAAC | CTGGAAGGAG | GGGCCTTAGA | GGTCCCAGTT | 9180 |
| GCTCAGTCAA | TGCCAGAGGT | GACAGAGCGA | GATGAGGATA | GAGCCCAAGC | AGGTGAACAA | 9240 |
| GACTCCATAG | AGGTGACCCT | TGGGTTAGAG | GCTGCCAGAA | CTGGACTGGA | ACTCGAGCAG | 9300 |
| GAAGTGGTAG | GGCTAGAGGA | CCCAAGGCAT | TTTGCCAGGG | AGGAGGCCAT | TCCCCATCC | 9360 |
| CTGGGGAGG | AAAGTGTGAA | GGCAAAGATA | GCTCAGGGCT | TGGAAGGGCC | TGGAAAGGAA | 9420 |
| CCAAAAGAGG | CAGGTGCTCT | GGACTCGGGG | ATCCTTGAAT | TGCCCAAGAC | TAGCAGCGAG | 9480 |
| GCTCTGGAAT | GCCAGGGCCA | TGAAGAGTCT | GAGTCCATGG | AGGGCTGGGA | AGAAGAGGAG | 9540 |
| GCCTCACTGG | AGACTTCAGA | TCATGAGGGC | AGTGATGCCC | CTCAGCCCAG | GCCCCAGAA | 9600 |
| ACAGAAGAAG | ATGAGGGTGC | ACAGGCAGCA | CTGACAGCCC | CTGGTCCCAA | GCTCTTGGAA | 9660 |
| CCCTGTTCAC | CCATCCCAAT | CCTGACAGAT | GCCCATGAGC | TGCAGCCCCA | GGCTGAGGGG | 9720 |
| ATCCAGGAGG | CTGGCTGGCA | GCCAGAAGCT | GGGTCTGAAG | CACTAGAAAG | GGTAGAAAAT | 9780 |
| GAGCCAGAGT | TTGGTCTTGG | GGAGATCCCG | GAGGGCCTCC | AGGATTGGGA | AGAGGGCAGA | 9840 |
| GAAGAAAGCG | AGGCAGATGA | TCTAGGGGAA | ACTCTCCCTG | ACTCTACTCC | CCTGGGCCTC | 9900 |
| TACCTGAGGT | CCCCTGCTTC | TCCAAAGTGG | GATCTGGCTG | GAGAACAGAG | GCTTTCCCCT | 9960 |
| CAAGGGGATG | CCGGGAAGGA | AGACTGGGGT | CCTGCTGTCC | CCGCTGCCCA | GGGCCTCAGT | 10020 |
| GGTCCACCGG | AAGAGGAGGA | GGAGCAAGGC | CATGGCTCTG | ACCTATCATC | TGAGGAGTTT | 10080 |
| GAGGACCTAG | GGACTGAGGC | CTCTCTTCTT | CCAGGGGTTC | CCAAGGAGGT | GGCAGATCAC | 10140 |
| GTGGGCCAAG | TGCCCCCGGT | ACTGCAGCCT | GCATGCTGGG | ATCAGGGTGG | GAATCTGAT | 10200 |
| GGGTTTGCTG | ATGAGGAAGA | AAGTGGGGAG | GAGGGAGAGG | AAGAAGATGC | TGATGAGGAA | 10260 |
| GGAGCAGAGT | CAGGAGCTCA | GTGGTGGGGG | TCAGGGCCT | CTGGTGGAGG | CTGCAAGGTC | 10320 |
| CAGGATATTG | CCCAAAGAGG | AGACCCGGTA | CAGGAGTCTG | TGGGTGTCAG | TGGTCTCTGG | 10380 |
| GATGATGGCT | TGAGAGGTGC | TGCAGCTAAT | GTTCCTGCCC | TAGAGATGGT | ATCTCAGGAC | 10440 |
| AGTGCTGAGC | CTTCTGGGTC | AGAGGAGTCT | GAGTCTGCTT | CCTTGGAGGG | GGAGGAAGGT | 10500 |
| CAAGTGACTG | ACCATTTAGA | TGCTCCCCAG | GAGGTGACCA | GCATGGTCCC | GGGGGTAGGA | 10560 |
| GATGCCTTTG | ACATTGGTGG | CCAGAGCCCC | AACTTGGACT | CAGAACAAGT | GAATGGGAAA | 10620 |
| ATGGAGAATG | GACTAGAACA | GGCTGAGGGG | CAGGTGGTCC | TGGATGGGGA | CGAGGATCAA | 10680 |
| GAACTCCTAT | TACAGGGACA | GGAGGTGGGT | GCTCTAAAGG | TTCCTTTGGT | AGCATCTCCT | 10740 |
| GTGCATCTAG | GCCCAAGCCA | GCCCCTGAAG | TTCACTCTGA | GTGGGGTAGA | TGGGGATTCC | 10800 |
| TGGTCCTCAG | GGGAAGACTA | GAAACTGCCC | CTCTGGCTCT | GAGGATGTAC | TGGTGGGGAT | 10860 |
| GTCCCTCCCT | GCTCTGGGTG | ACCACTCTTA | GCTTTGATAA | CTTGACCCAT | GGTATTTGTC | 10920 |
| CTGGAGAGTT | GTGGCTGGGC | TGAGCAAGGG | AGGTGAGATC | CTCCTGAAGG | CTCAGGAGTT | 10980 |
| CCAGGCCTAT | AGTTCTACCC | CCTCTTTCTT | CTGTGGCTCA | CCTGCTGGAA | GAGGCCTGGG | 11040 |
| CCCAGAGCTT | TCCCACAAGG | CTGTTCTGGC | CACAGCTTGC | TAGCCTTGCC | TACCACCTGC | 11100 |
| ACAAGGTCTG | GTCTGGTGTA | TGACCAGGGG | AGCTGAGGGC | AGCATTTATC | TGACCCTTCA | 11160 |
| TCTCAGCCTG | CTGAGAGCTT | GTTCCTCTCT | TCCTCCCTGA | ATAAAGCCGT | ATCCCTACCT | 11220 |
| ACAAAAAAAA | AAAAAA | | | | | 11236 |

( 2 ) INFORMATION FOR SEQ ID NO:2:

( i ) SEQUENCE CHARACTERISTICS:
   ( A ) LENGTH: 1805 amino acids
   ( B ) TYPE: amino acid
   ( D ) TOPOLOGY: linear ( i i ) MOLECULE TYPE: protein ( x i ) SEQUENCE DESCRIPTION: SEQ ID NO:2:

```
Met Glu Gly Cys Val Gly Glu Glu Ser Phe Gln Met Trp Glu Leu Asn
  1               5                  10                  15

Arg Arg Leu Glu Ala Tyr Leu Thr Arg Val Lys Thr Leu Glu Glu Gln
              20                  25                  30

Asn Gln Leu Leu Ser Ala Glu Leu Gly Gly Leu Arg Ala Gln Ser Gly
          35                  40                  45

Asp Thr Ser Trp Arg Ala Arg Ala Asp Asp Glu Leu Ala Ser Leu Arg
 50                  55                  60

Ile Leu Val Asp Gln Arg Trp Arg Glu Lys Leu Glu Ala Glu Val Gln
 65                  70                  75                  80

Arg Asp Asn Leu Ala Glu Glu Leu Glu Ser Val Ala Gly Arg Cys Gln
              85                  90                  95

Gln Val Arg Leu Ala Arg Glu Arg Thr Val Gln Glu Ala Ala Cys Ser
             100                 105                 110

Arg Arg Ala Leu Glu Ala Glu Lys Asn Ala Arg Gly Trp Leu Ser Thr
             115                 120                 125

Gln Ala Ala Glu Leu Glu Arg Glu Leu Glu Ala Leu Arg Ala Ala His
       130                 135                 140

Glu Glu Glu Arg Ala His Leu Asn Ala Gln Ala Ala Cys Ala Pro Arg
145                 150                 155                 160

Arg Pro Pro Ala Pro Pro His Arg Ile Pro Gly Pro Ala Pro Glu Val
                 165                 170                 175

Glu Asp Leu Ala Arg Arg Leu Gly Glu Val Trp Arg Gly Ala Val Arg
             180                 185                 190

Asp Tyr Gln Glu Arg Val Ala His Met Glu Ser Ser Leu Gly Gln Ala
             195                 200                 205

Arg Glu Arg Leu Ser Gln Ala Val Arg Gly Ala Arg Glu Cys Arg Leu
210                 215                 220

Glu Val Gln Gln Leu Gln Ala Asp Arg Asp Ser Leu Gln Glu Arg Arg
225                 230                 235                 240

Glu Ala Leu Glu Gln Arg Leu Glu Gly Arg Trp Gln Asp Arg Leu Gln
             245                 250                 255

Ala Thr Asp Lys Phe Gln Leu Ala Val Glu Ala Leu Glu Gln Glu Lys
             260                 265                 270

Gln Gly Leu Gln Ser Gln Ile Ala Gln Ile Leu Glu Gly Gly Gln Gln
             275                 280                 285

Leu Ala His Leu Lys Met Ser Leu Ser Leu Glu Val Ala Thr Tyr Arg
290                 295                 300

Thr Leu Leu Glu Ala Glu Asn Ser Arg Leu Gln Thr Pro Gly Arg Gly
305                 310                 315                 320

Ser Gln Ala Ser Leu Gly Phe Leu Asp Pro Lys Leu Lys Pro Asn Phe
                 325                 330                 335

Leu Gly Ile Pro Glu Asp Gln Tyr Leu Gly Ser Val Leu Pro Ala Leu
             340                 345                 350

Ser Pro Thr Ser Phe Pro Ser Pro Leu Pro Asn Thr Leu Glu Thr Pro
             355                 360                 365

Val Thr Ala Phe Leu Lys Thr Gln Glu Phe Leu Gln Ala Arg Thr Pro
370                 375                 380
```

-continued

| | | | | | | | | | | | | | | |
|---|---|---|---|---|---|---|---|---|---|---|---|---|---|---|
| Thr | Leu | Ala | Ser | Thr | Pro | Ile | Pro | Pro | Ile | Ser | Glu | Ala | Pro | Cys | Pro |
| 385 | | | | 390 | | | | | 395 | | | | | 400 |
| Pro | Asn | Ala | Glu | Val | Arg | Ala | Gln | Glu | Val | Pro | Leu | Ser | Leu | Leu | Gln |
| | | | | 405 | | | | 410 | | | | | 415 | | |
| Thr | Gln | Ala | Pro | Glu | Pro | Leu | Trp | Leu | Lys | Ala | Thr | Val | Pro | Ser | Ser |
| | | | 420 | | | | 425 | | | | | 430 | | | |
| Ser | Ala | Ile | Leu | Pro | Glu | Leu | Glu | Glu | Pro | Gly | Gly | Lys | Gln | Gln | Gly |
| | | 435 | | | | 440 | | | | | 445 | | | | |
| His | Phe | Pro | Asp | Asp | Leu | Thr | Ser | Leu | Ala | Thr | Asn | Leu | Asn | Pro | His |
| | 450 | | | | 455 | | | | | 460 | | | | | |
| His | Pro | Thr | Leu | Glu | Ala | Lys | Asp | Gly | Glu | Ser | Ser | Glu | Ser | Arg | Val |
| 465 | | | | 470 | | | | | 475 | | | | | 480 | |
| Ser | Ser | Ile | Phe | Gln | Glu | Asp | Glu | Gly | Gln | Ile | Trp | Glu | Leu | Val | Glu |
| | | | 485 | | | | | 490 | | | | | 495 | | |
| Lys | Glu | Ala | Asp | Ile | Glu | Val | Lys | Val | Glu | Asn | Ser | Ser | Ala | Gln | Lys |
| | | | 500 | | | | 505 | | | | | 510 | | | |
| Thr | Gln | Glu | Ser | Gly | Leu | Asp | Thr | Glu | Glu | Thr | Gln | Asp | Ser | Gln | Gly |
| | | 515 | | | | 520 | | | | | 525 | | | | |
| Pro | Leu | Gln | Lys | Glu | Thr | Leu | Lys | Ala | Leu | Gly | Glu | Glu | Pro | Leu | Met |
| | 530 | | | | 535 | | | | | 540 | | | | | |
| Ser | Leu | Lys | Ile | Gln | Asn | Tyr | Glu | Thr | Ala | Gly | Lys | Glu | Asn | Cys | Asn |
| 545 | | | | 550 | | | | | 555 | | | | | 560 | |
| Ser | Ser | Thr | Glu | Gly | His | Leu | Gly | Thr | Leu | Glu | Gly | Pro | Glu | Lys | Glu |
| | | | 565 | | | | | 570 | | | | | 575 | | |
| Lys | Gln | Ile | Pro | Leu | Lys | Ser | Leu | Glu | Glu | Lys | Asn | Val | Glu | Ser | Glu |
| | | | 580 | | | | | 585 | | | | | 590 | | |
| Lys | Thr | Leu | Glu | Asn | Gly | Val | Pro | Val | Leu | Ser | Glu | Leu | Leu | Gly | Lys |
| | 595 | | | | | 600 | | | | | 605 | | | | |
| Glu | Asp | Thr | Arg | Thr | Glu | Asp | Gln | Glu | Leu | Met | Ser | Pro | Lys | Gly | Thr |
| | 610 | | | | 615 | | | | | 620 | | | | | |
| Leu | Lys | Arg | Phe | Ser | Ser | Leu | Gly | Lys | Glu | Ser | Gln | Glu | Val | Val | Arg |
| 625 | | | | | 630 | | | | | 635 | | | | | 640 |
| Pro | Ser | Lys | Glu | Gly | Asn | Leu | Glu | Ser | Trp | Thr | Ala | Phe | Lys | Glu | Glu |
| | | | | 645 | | | | | 650 | | | | | 655 | |
| Ser | Gln | His | Pro | Leu | Gly | Phe | Pro | Gly | Ala | Glu | Asp | Gln | Met | Leu | Glu |
| | | | 660 | | | | | 665 | | | | | 670 | | |
| Arg | Leu | Val | Glu | Lys | Glu | Asp | Gln | Ser | Phe | Pro | Arg | Ser | Pro | Glu | Glu |
| | | | 675 | | | | 680 | | | | | 685 | | | |
| Glu | Asp | Gln | Glu | Ala | Cys | Arg | Pro | Leu | Gln | Lys | Glu | Asn | Gln | Glu | Pro |
| | 690 | | | | | 695 | | | | | 700 | | | | |
| Leu | Gly | Tyr | Glu | Glu | Ala | Glu | Gly | Gln | Ile | Leu | Glu | Arg | Leu | Ile | Glu |
| 705 | | | | | 710 | | | | | 715 | | | | | 720 |
| Lys | Glu | Ser | Gln | Glu | Ser | Leu | Arg | Ser | Pro | Glu | Glu | Glu | Asp | Gln | Glu |
| | | | | 725 | | | | | 730 | | | | | 735 | |
| Ala | Gly | Arg | Ser | Leu | Gln | Lys | Glu | Asn | Gln | Glu | Pro | Leu | Gly | Tyr | Glu |
| | | | 740 | | | | | 745 | | | | | 750 | | |
| Glu | Ala | Glu | Asp | Gln | Met | Leu | Glu | Arg | Leu | Ile | Glu | Lys | Glu | Ser | Gln |
| | | | 755 | | | | | 760 | | | | | 765 | | |
| Glu | Ser | Leu | Lys | Ser | Pro | Glu | Glu | Asn | Gln | Arg | Ile | Gly | Lys | Pro | Leu |
| | 770 | | | | | 775 | | | | | 780 | | | | |
| Glu | Arg | Glu | Asn | Gln | Lys | Ser | Leu | Arg | Tyr | Leu | Glu | Glu | Asn | Gln | Glu |
| 785 | | | | | 790 | | | | | 795 | | | | | 800 |
| Thr | Phe | Val | Pro | Leu | Glu | Ser | Arg | Asn | Gln | Arg | Pro | Leu | Arg | Ser | Leu |
| | | | | 805 | | | | | 810 | | | | | 815 | |
| Glu | Val | Glu | Glu | Glu | Glu | Gln | Arg | Ile | Val | Lys | Pro | Leu | Glu | Lys | Val |

-continued

|     |     |     | 820 |     |     |     | 825 |     |     |     | 830 |     |
| --- | --- | --- | --- | --- | --- | --- | --- | --- | --- | --- | --- | --- |

Ser Gln Asp Ser Leu Gly Ser Leu Ala Glu Glu Asn Val Gln Pro Leu
          835             840              845

Arg Tyr Leu Glu Glu Asp Asp Cys Ile Asn Lys Ser Leu Leu Glu Asp
    850             855                 860

Lys Thr His Lys Ser Leu Gly Ser Leu Glu Asp Arg Asn Gly Asp Ser
865             870              875                      880

Ile Ile Ile Pro Gln Glu Ser Glu Thr Gln Val Ser Leu Arg Pro Pro
                885             890                      895

Glu Glu Glu Asp Gln Arg Ile Val Asn His Leu Glu Lys Glu Ser Gln
            900              905              910

Glu Phe Ser Arg Ser Ser Glu Glu Glu Gln Val Met Glu Arg Ser
        915             920              925

Leu Glu Gly Glu Asn His Glu Ser Leu Ser Ser Val Glu Lys Glu Asp
    930             935              940

Gln Met Val Glu Ser Gln Leu Glu Lys Glu Ser Gln Asp Ser Gly Lys
945             950              955                      960

Ser Leu Glu Asp Glu Ser Gln Glu Thr Phe Gly Pro Leu Glu Lys Glu
            965             970              975

Asn Ala Glu Ser Leu Arg Ser Leu Ala Gly Gln Asp Gln Glu Glu Gln
            980             985              990

Lys Leu Glu Gln Glu Thr Gln Gln Thr Leu Arg Ala Val Gly Asn Glu
        995             1000             1005

Gln Met Ala Val Ser Pro Glu Lys Val Asp Pro Glu Leu Pro Lys
    1010            1015             1020

Pro Leu Gly Asn Asp Gln Glu Ile Ala Arg Ser Leu Gly Lys Glu Asn
1025            1030             1035                    1040

Gln Glu Ser Leu Val Ser Leu Lys Glu Lys Gly Ile Glu Thr Val Lys
            1045             1050             1055

Ser Leu Glu Thr Glu Ile Ile Glu Pro Leu Glu Thr Ala Glu Glu Asp
            1060             1065             1070

Leu Glu Arg Arg Lys Ser Ile Asp Thr Gln Glu Pro Leu Trp Ser Thr
        1075             1080             1085

Glu Val Ala Arg Glu Thr Val Glu Pro Pro Glu Asp Glu Pro Pro Gly
    1090             1095             1100

Ser Leu Gly Ser Val Asp Glu Asn Arg Glu Thr Leu Thr Ser Leu Glu
1105            1110             1115                    1120

Lys Glu Ser Gln Glu Leu Ser Ser Leu Gly Lys Trp Asn Val Glu Thr
            1125             1130             1135

Arg Val Glu Asp Ser Gln Gln Cys Leu Gln Val Glu Glu Gly Leu Gln
        1140             1145             1150

Glu Glu Gln His Gln Glu Ser Leu Arg Glu Val Lys Gln Glu Leu Pro
        1155             1160             1165

Ser Ser Gly Asn Gln Gln Arg Trp Glu Asp Val Val Glu Gly Lys Ala
    1170             1175             1180

Val Gly Gln Glu Ala Pro Leu Ala Thr Thr Gly Val Gly Thr Glu Asp
1185             1190             1195                    1200

Lys Ala Glu Leu His Leu Arg Gly Gln Gly Gly Glu Glu Ala Ala
            1205             1210             1215

Ala Glu Gly Glu Leu Leu Gln Asp Ile Val Gly Glu Ala Trp Ser Leu
        1220             1225             1230

Gly Ser Ser Glu Pro Lys Glu Gln Arg Val Pro Ala Glu Ala Leu Asp
    1235             1240             1245

Asn Leu Glu Gly Gly Ala Leu Glu Val Pro Val Ala Gln Ser Met Pro
1250             1255             1260

```
Glu Val Thr Glu Arg Asp Glu Asp Arg Ala Gln Ala Gly Glu Gln Asp
1265                1270                1275                1280

Ser Ile Glu Val Thr Leu Gly Leu Glu Ala Ala Arg Thr Gly Leu Glu
                1285                1290                1295

Leu Glu Gln Glu Val Val Gly Leu Glu Asp Pro Arg His Phe Ala Arg
            1300                1305                1310

Glu Glu Ala Ile Pro Pro Ser Leu Gly Glu Glu Ser Val Lys Ala Lys
        1315                1320                1325

Ile Ala Gln Gly Leu Glu Gly Pro Gly Lys Glu Pro Lys Glu Ala Gly
    1330                1335                1340

Ala Leu Asp Ser Gly Ile Leu Glu Leu Pro Lys Thr Ser Ser Glu Ala
1345                1350                1355                1360

Leu Glu Cys Gln Gly His Glu Glu Ser Glu Ser Met Glu Gly Trp Glu
                1365                1370                1375

Glu Glu Glu Ala Ser Leu Glu Thr Ser Asp His Glu Gly Ser Asp Ala
            1380                1385                1390

Pro Gln Pro Arg Pro Pro Glu Thr Glu Glu Asp Glu Gly Ala Gln Ala
        1395                1400                1405

Ala Leu Thr Ala Pro Gly Pro Lys Leu Leu Glu Pro Cys Ser Pro Ile
    1410                1415                1420

Pro Ile Leu Thr Asp Ala His Glu Leu Gln Pro Gln Ala Glu Gly Ile
1425                1430                1435                1440

Gln Glu Ala Gly Trp Gln Pro Glu Ala Gly Ser Glu Ala Leu Glu Arg
                1445                1450                1455

Val Glu Asn Glu Pro Glu Phe Gly Leu Gly Glu Ile Pro Glu Gly Leu
            1460                1465                1470

Gln Asp Trp Glu Glu Gly Arg Glu Glu Ser Glu Ala Asp Asp Leu Gly
        1475                1480                1485

Glu Thr Leu Pro Asp Ser Thr Pro Leu Gly Leu Tyr Leu Arg Ser Pro
    1490                1495                1500

Ala Ser Pro Lys Trp Asp Leu Ala Gly Glu Gln Arg Leu Ser Pro Gln
1505                1510                1515                1520

Gly Asp Ala Gly Lys Glu Asp Trp Gly Pro Ala Val Pro Ala Ala Gln
                1525                1530                1535

Gly Leu Ser Gly Pro Pro Glu Glu Glu Glu Gln Gly His Gly Ser
            1540                1545                1550

Asp Leu Ser Ser Glu Glu Phe Glu Asp Leu Gly Thr Glu Ala Ser Leu
        1555                1560                1565

Leu Pro Gly Val Pro Lys Glu Val Ala Asp His Val Gly Gln Val Pro
    1570                1575                1580

Pro Val Leu Gln Pro Ala Cys Trp Asp Gln Gly Gly Glu Ser Asp Gly
1585                1590                1595                1600

Phe Ala Asp Glu Glu Glu Ser Gly Glu Glu Gly Glu Glu Glu Asp Ala
                1605                1610                1615

Asp Glu Glu Gly Ala Glu Ser Gly Ala Gln Trp Trp Gly Ser Gly Ala
            1620                1625                1630

Ser Gly Gly Gly Cys Lys Val Gln Asp Ile Ala Gln Arg Gly Asp Pro
        1635                1640                1645

Val Gln Glu Ser Val Gly Val Ser Gly Leu Trp Asp Asp Gly Leu Arg
    1650                1655                1660

Gly Ala Ala Ala Asn Val Pro Ala Leu Glu Met Val Ser Gln Asp Ser
1665                1670                1675                1680

Ala Glu Pro Ser Gly Ser Glu Glu Ser Glu Ser Ala Ser Leu Glu Gly
                1685                1690                1695
```

-continued

```
        Glu Glu Gly Gln Val Thr Asp His Leu Asp Ala Pro Gln Glu Val Thr
                    1700                1705                1710

Ser Met Val Pro Gly Val Gly Asp Ala Phe Asp Ile Gly Gly Gln Ser
                    1715                1720                1725

Pro Asn Leu Asp Ser Glu Gln Val Asn Gly Lys Met Glu Asn Gly Leu
                    1730                1735                1740

Glu Gln Ala Glu Gly Gln Val Val Leu Asp Gly Asp Glu Asp Gln Glu
        1745                1750                1755                1760

Leu Leu Leu Gln Gly Gln Glu Val Gly Ala Leu Lys Val Pro Leu Val
                    1765                1770                1775

Ala Ser Pro Val His Leu Gly Pro Ser Gln Pro Leu Lys Phe Thr Leu
                    1780                1785                1790

Ser Gly Val Asp Gly Asp Ser Trp Ser Ser Gly Glu Asp
                    1795                1800                1805
```

( 2 ) INFORMATION FOR SEQ ID NO:3:

( i ) SEQUENCE CHARACTERISTICS:
        ( A ) LENGTH: 4852 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:3:

```
ATGGAGGGCT GCATGGGGGA GGAGTCGTTT CAGATGTGGG AGCTCAATCG GCGCCTGGAG    60
GCCTACCTGG GCCGGGTCAA GGCGCTGGAG GAGCAGAATG AGCTGCTCAG CGCCGGACTC   120
GGGGGGCTCC GGCGACAATC CGCGGACACC TCCTGGCGGG CGCATGCCGA CGACGAGCTG   180
GCGGCCCTGC GTGCGCTCGT TGACCAACGC TGGCGGGAGA AGCACGCGGC CGAGGTGGCG   240
CGCGACAACC TGGCTGAAGA GCTGGAGGGC GTGGCAGGCC GATGCGAGCA GCTGCGGCTG   300
GCCCGGGAGC GGACGACGGA GGAGGTAGCC CGCAACCGGC GCGCCGTCGA GGCAGAGAAA   360
TGCGCCCGGG CCTGGCTGAG TAGCCAGGGG GCAGAGCTGG AGCGCGAGCT AGAGGCTCTA   420
CGCGTGGCGC ACGAGGAGGA GCGCGTCGGT CTGAACGCGC AGGCTGCCTG TGCCCCCCGC   480
CTGCCGCGC CGCCCCGGCC TCCCGCGCCG GCCCCGGAGG TAGAGGAGCT GGCAAGGCGA    540
CTGGGCGAGG CGTGGCGCGG GGCAGTGCGC GGCTACCAGG AGCGCGTGGC ACACATGGAG   600
ACGTCGCTGG ACCAGACCCG CGAGCGCCTG GCCCGGGCGG TGCAGGGTGC CGCGAGGTC    660
CGCCTGGAGC TACAGCAGCT CCAGGCTGAG CGCGGAGGCC TCCTGGAGCG CAGGGCAGCG   720
TTGAACAGA GGTTGGAGGG CCGCTGGCAG GAGCGGCTGC GGGCTACTGA AAAGTTCCAG    780
CTGGCTGTGG AGGCCCTGGA GCAGGAGAAA CAGGGCCTAC AGAGCCAGAT CGCTCAGGTC   840
CTGGAAGGTC GGCAGCAGCT GGCGCACCTC AAGATGTCCC TCAGCCTGGA GGTGGCCACG   900
TACAGGACCC TCCTGGAGGC TGAGAACTCC CGGCTGCAAA CACCTGGCGG TGGCTCCAAG   960
ACTTCCCTCA GCTTTCAGGA CCCCAAGCTG GAGCTGCAAT TCCCTAGGAC CCCAGAGGGC  1020
CGGCGTCTTG GATCTTTGCT CCCAGTCCTG AGCCCAACTT CCCTCCCCTC ACCCTTGCCT  1080
GCTACCCTTG AGACACCTGT GCCAGCCTTT CTTAAGAACC AAGAATTCCT CCAGGCCCGT  1140
ACCCCTACCT TGGCCAGCAC CCCCATCCCC CCACACCTC AGGCACCCTC TCCTGCTGTA   1200
GATGCAGAGA TCAGAGCCCA GGATGCTCCT CTCTCTCTGC TCCAGACACA GGGTGGGAGG  1260
AAACAGGCTC CAGAGCCCCT GCGGGCTGAA GCCAGGGTGG CCATTCCTGC CAGCGTCCTG  1320
CCTGGACCAG AGGAGCCTGG GGGCCAGCGG CAAGAGGCCA GTACAGGCCA GTCCCCAGAG  1380
GACCATGCCT CCTTGGCACC ACCCCTCAGC CCTGACCACT CCAGTTTAGA GGCTAAGGAT  1440
```

```
GGAGAATCCG GTGGGTCTAG AGTGTTCAGC ATATGCCGAG GGGAAGGTGA AGGGCAAATC      1500
TGGGGGTTGG TAGAGAAAGA AACAGCCATA GAGGGCAAAG TGGTAAGCAG CTTGCAGCAG      1560
GAAATATGGG AAGAAGAGGA TCTAAACAGG AAGGAAATCC AGGACTCCCA GGTTCCTTTG      1620
GAAAAGAAA  CCCTGAAGTC TCTGGGAGAG GAGATTCAAG AGTCACTGAA GACTCTGGAA      1680
AACCAGAGCC ATGAGACACT AGAAAGGGAG AATCAAGAAT GTCCGAGGTC TTTAGAAGAA      1740
GACTTAGAAA CACTAAAAAG TCTAGAAAAG GAAATAAAA  GAGCTATTAA AGGATGTGGA      1800
GGTAGTGAGA CCTCTAGAAA AAGAGGCTGT AGGCAACTTA AGCCTACAGG AAAAGAGGAC      1860
ACACAGACAT TGCAATCCCT GCAAAGGAG  AATCAAGAAC TAATGAAATC TCTTGAAGGT      1920
AATCTAGAGA CATTTTTATT TCCAGGAACG GAAAATCAAG AATTAGTAAG TTCTCTGCAA      1980
GAGAACTTAG AGTCATTGAC AGCTCTGGAA AAGGAGAATC AAGAGCCACT GAGATCTCCA      2040
GAAGTAGGGG ATGAGGAGGC ACTGAGACCT CTGACAAAGG AGAATCAGGA ACCCCTGAGG      2100
TCTCTTGAAG ATGAGAACAA AGAGGCCTTT AGATCTCTAG AAAAGAGAA  CCAGGAGCCA      2160
CTGAAGACTC TAGAAGAAGA GGACCAGAGT ATTGTGAGAC TCTAGAAAC  AGAGAATCAC      2220
AAATCACTGA GGTCTTTAGA AGAACAGGAC CAAGAGACAT TGAGAACTCT TGAAAAGAG       2280
ACTCAACAGC GACGGAGGTC TCTAGGGAA  CAGGATCAGA TGACATTAAG ACCCCCAGAA      2340
AAAGTGGATC TAGAACCACT GAAGTCTCTT GACCAGGAGA TAGCTAGACC TCTTGAAAAT      2400
GAGAATCAAG AGTTCTTAAA GTCACTCAAA GAAGAGAGCG TAGAGGCAGT AAAATCTTTA      2460
GAAACAGAGA TCCTAGAATC ACTGAAGTCT GCGGGACAAG AGAACCTGGA AACACTGAAA      2520
TCTCCAGAAA CTCAAGCACC ACTGTGGACT CCAGAAGAAA TAAATAAATC AGGGGGCAAT      2580
GAATCCTCTA GAAAGGAAA  TTCAAGAACC ACTGGAGTCT GTGGAAGTGA ACCAAGAGAC      2640
ATTCAGACTC CTGGAAGAGG AGAATCAGGA ATCATTGAGA TCTCTGGGAG CATGGAACCT      2700
GGAGAATTTG AGATCTCCAG AGGAGTAGAC AAGGAAAGTC AAAGGAATCT GGAAGAGGAA      2760
GAGAACCTGG GAAAGGGAGA GTACCAAGAG TCACTGAGGT CTCTGGAGGA GGAGGGACAG      2820
GAGCTGCCGC AGTCTGCAGA TGTGCAGAGG TGGAAGATA  CGGTGGAGAA GGACCAAGAA      2880
CTGGCTCAGG AAAGCCCTCC TGGGATGGCT GGAGTGGAAA ATAAGGATGA GGCAGAGCTG      2940
AATCTAAGGG AGCAGGATGG CTTCACTGGG AAGGAGGAGG TGGTAGAGCA GGGAGAGCTG      3000
AATGCCACAG AGGAGGTCTG GTTCCCAGGC GAGGGCACC  CAGAGAACCC TGAGCCCAAA      3060
GAGCAGAGAG GCCTGGTTGA GGGAGCCAGT GTGAAGGGAG GGGCTGAGGG CCTCCAGGAC      3120
CCTGAAGGGC AATCACAACA GGTGGGGACC CCAGGCCTCC AGGCTCCCCA GGGGCTGCCA      3180
GAGGCGATAG AGCCCCTGGT GGAAGATGAT GTGGCCCCAG GGGTGACCA  AGCCTCCCCA      3240
GAGGTCATGT TGGGGTCAGA GCCTGCCATG GGTGAGTCTG CTGCGGGAGC TGAGCCAGGC      3300
CTGGGGCAGG GGGTGGGAGG GCTGGGGGAC CCAGGCCATC TGACCAGGGA AGAGGTGATG      3360
GAACCACCCC TGGAAGAGGA GAGTTTGGAG GCAAAGAGGG TTCAGGGCTT GGAAGGGCCT      3420
AGAAAGGACC TAGAGGAGGC AGGTGGTCTG GGGACAGAGT TCTCCGAGCT GCCTGGGAAG      3480
AGCAGAGACC CTTGGGAGCC TCCCAGGGAG GGTAGGGAGG AGTCAGAGGC TGAGGCCCCC      3540
AGGGGAGCAG AGGAGGCGTT CCCTGCTGAG ACCCTGGGCC ACACTGGAAG TGATGCCCCT      3600
TCACCTTGGC CTCTGGGGTC AGAGGAAGCT GAGGAGGATG TACCACCAGT GCTGGTCTCC      3660
CCCAGCCCAA CGTACACCCC GATCCTGGAA GATGCCCCTG GCTCAGCCT  CAGGCTGAAG      3720
GGAGTCAGGA GGCTAGCTGG GGGGTGCAGG GGAGGGCTGA AGCTGGGAAA GTAGAGAGCG      3780
AGCAGGAGGA GTTGGGTTCT GGGGAGATCC CCGAGGGCCT CCAGGAGGAA GGGGAGGAGA      3840
GCAGAGAAGA GAGCGAGGAG GATGAGCTCG GGAGACCCT  TCCAGACTCC ACTCCCCTGG      3900
```

```
GCTTCTACCT CAGGTCCCCC ACCTCCCCCA GGTGGACCCC ACTGGAGAGC AGAGGCCACC    3960

CCCTCAAGGA GACTGGAAAG GAGGGCTGGG ATCCTGCTGT CCTGGCTTCC GAGGGCCTTG    4020

AGGACCCTCA GAAAAGGAGG AGGGGGAGGA GGGAGAAGAG GAGTGTGGCC GTGACTCTGA    4080

CCTGTCAGAA GAATTTGAGG ACCTGGGGAC TGAGGCACCT TTTCTTCCTG GGGTCCCTGG    4140

GGAGGTGGCA GAACCTCTGG GCCAGGTGCC CCAGCTGCTA CTGGATCCTG CAGCCTGGGA    4200

TCGAGATGGG GAGTCTGATG GGTTTGCAGA TGAGGAAGAA AGTGGGGAGG AGGGAGAGGA    4260

GGATCAGGAG GAGGGGAGGG AGCCAGGGGC TGGGCGGTGG GGCCAGGGT CTTCTGTTGG     4320

CAGCCTCCAG GCCCTGAGTA GCTCCCAGAG AGGGGAATTC CTGGAGTCTG ATTCTGTAAG    4380

TGTCAGCGTC CCCTGGGATG ACAGCTTGAG GGGTGCAGTG GCTGGTGCCC CCAAGACTGC    4440

CCTGGAAACG GAGTCCCAGG ACAGTGCTGA GCCTTCTGGC TCAGAGGAAG AGTCTGACCC    4500

TGTTTCCTTG GAGAGGGAGG ACAAAGTCCC TGGCCCTCTA GAGATCCCCA GTGGGATGGA    4560

GGATGCAGGC CCAGGGGCAG ACATCATTGG TGTTAATGGC CAGGGTCCCA ACTTGGAGGG    4620

GAAGTCACAG CATGTAAATG GGGGAGTAAT GAACGGGCTG GAGCAGTCTG AGGAAAGTGG    4680

GGCAAGGAAT GCGCTAGTCT CTGAGGGAGA CCGAGGGAGC CCCTTTCAGG AGGAGGAGGG    4740

GAGTGCTCTG AAGAGGTCTT CGGCAGGGGC TCCTGTTCAC CTGGGCCAGG GTCAGTTCCT    4800

GAAGTTCACT CAGAGGGAAG GAGATAGAGA GTCCTGGTCC TCAGGGGAGG AC            4852
```

( 2 ) INFORMATION FOR SEQ ID NO:4:

( i ) SEQUENCE CHARACTERISTICS:
        ( A ) LENGTH: 1618 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Glu Gly Cys Met Gly Glu Glu Ser Phe Gln Met Trp Glu Leu Asn
 1               5                  10                  15

Arg Arg Leu Glu Ala Tyr Leu Gly Arg Val Lys Ala Leu Glu Glu Gln
             20                  25                  30

Asn Glu Leu Leu Ser Ala Gly Leu Gly Gly Leu Arg Arg Gln Ser Ala
         35                  40                  45

Asp Thr Ser Trp Arg Ala His Ala Asp Asp Glu Leu Ala Ala Leu Arg
     50                  55                  60

Ala Leu Val Asp Gln Trp Arg Glu Lys His Ala Ala Glu Val Ala
 65                  70                  75                  80

Arg Asp Asn Leu Ala Glu Glu Leu Glu Gly Val Ala Gly Arg Cys Glu
                 85                  90                  95

Gln Leu Arg Leu Ala Arg Glu Arg Thr Thr Glu Glu Val Ala Arg Asn
            100                 105                 110

Arg Arg Ala Val Glu Ala Glu Lys Cys Ala Arg Ala Trp Leu Ser Ser
        115                 120                 125

Gln Gly Ala Glu Leu Glu Arg Glu Leu Glu Ala Leu Arg Val Ala His
    130                 135                 140

Glu Glu Glu Arg Val Gly Leu Asn Ala Gln Ala Ala Cys Ala Pro Arg
145                 150                 155                 160

Leu Pro Ala Pro Pro Arg Pro Pro Ala Pro Ala Pro Glu Val Glu Glu
                165                 170                 175

Leu Ala Arg Arg Leu Gly Glu Ala Trp Arg Gly Ala Val Arg Gly Tyr
            180                 185                 190

Gln Glu Arg Val Ala His Met Glu Thr Ser Leu Asp Gln Thr Arg Glu
                195                 200                 205
```

-continued

| Arg | Leu | Ala | Arg | Ala | Val | Gln | Gly | Ala | Arg | Glu | Val | Arg | Leu | Glu | Leu |
|-----|-----|-----|-----|-----|-----|-----|-----|-----|-----|-----|-----|-----|-----|-----|-----|
| | 210 | | | | 215 | | | | | 220 | | | | | |
| Gln | Gln | Leu | Gln | Ala | Glu | Arg | Gly | Gly | Leu | Leu | Glu | Arg | Arg | Ala | Ala |
| 225 | | | | | 230 | | | | | 235 | | | | | 240 |
| Leu | Glu | Gln | Arg | Leu | Glu | Gly | Arg | Trp | Gln | Glu | Arg | Leu | Arg | Ala | Thr |
| | | | | 245 | | | | | 250 | | | | | | 255 |
| Glu | Lys | Phe | Gln | Leu | Ala | Val | Glu | Ala | Leu | Glu | Gln | Glu | Lys | Gln | Gly |
| | | | | 260 | | | | 265 | | | | | 270 | | |
| Leu | Gln | Ser | Gln | Ile | Ala | Gln | Val | Leu | Glu | Gly | Arg | Gln | Gln | Leu | Ala |
| | | | 275 | | | | 280 | | | | | 285 | | | |
| His | Leu | Lys | Met | Ser | Leu | Ser | Leu | Glu | Val | Ala | Thr | Tyr | Arg | Thr | Leu |
| | | | 290 | | | | 295 | | | | 300 | | | | |
| Leu | Glu | Ala | Glu | Asn | Ser | Arg | Leu | Gln | Thr | Pro | Gly | Gly | Gly | Ser | Lys |
| 305 | | | | | 310 | | | | | 315 | | | | | 320 |
| Thr | Ser | Leu | Ser | Phe | Gln | Asp | Pro | Lys | Leu | Glu | Leu | Gln | Phe | Pro | Arg |
| | | | | 325 | | | | | 330 | | | | | | 335 |
| Thr | Pro | Glu | Gly | Arg | Arg | Leu | Gly | Ser | Leu | Leu | Pro | Val | Leu | Ser | Pro |
| | | | | 340 | | | | 345 | | | | | 350 | | |
| Thr | Ser | Leu | Pro | Ser | Pro | Leu | Pro | Ala | Thr | Leu | Glu | Thr | Pro | Val | Pro |
| | | | | 355 | | | | 360 | | | | | 365 | | |
| Ala | Phe | Leu | Lys | Asn | Gln | Glu | Phe | Leu | Gln | Ala | Arg | Thr | Pro | Thr | Leu |
| | 370 | | | | | 375 | | | | | 380 | | | | |
| Ala | Ser | Thr | Pro | Ile | Pro | Pro | Thr | Pro | Gln | Ala | Pro | Ser | Pro | Ala | Val |
| 385 | | | | | 390 | | | | | 395 | | | | | 400 |
| Asp | Ala | Glu | Ile | Arg | Ala | Gln | Asp | Ala | Pro | Leu | Ser | Leu | Leu | Gln | Thr |
| | | | | 405 | | | | | 410 | | | | | | 415 |
| Gln | Gly | Gly | Arg | Lys | Gln | Ala | Pro | Glu | Pro | Leu | Arg | Ala | Glu | Ala | Arg |
| | | | 420 | | | | | 425 | | | | | 430 | | |
| Val | Ala | Ile | Pro | Ala | Ser | Val | Leu | Pro | Gly | Pro | Glu | Glu | Pro | Gly | Gly |
| | | 435 | | | | | 440 | | | | | 445 | | | |
| Gln | Arg | Gln | Glu | Ala | Ser | Thr | Gly | Gln | Ser | Pro | Glu | Asp | His | Ala | Ser |
| | 450 | | | | | 455 | | | | | 460 | | | | |
| Leu | Ala | Pro | Pro | Leu | Ser | Pro | Asp | His | Ser | Ser | Leu | Glu | Ala | Lys | Asp |
| 465 | | | | | 470 | | | | | 475 | | | | | 480 |
| Gly | Glu | Ser | Gly | Gly | Ser | Arg | Val | Phe | Ser | Ile | Cys | Arg | Gly | Glu | Gly |
| | | | | 485 | | | | | 490 | | | | | 495 | |
| Glu | Gly | Gln | Ile | Trp | Gly | Leu | Val | Glu | Lys | Glu | Thr | Ala | Ile | Glu | Gly |
| | | | 500 | | | | | 505 | | | | | 510 | | |
| Lys | Val | Val | Ser | Ser | Leu | Gln | Gln | Glu | Ile | Trp | Glu | Glu | Asp | Leu |
| | | 515 | | | | | 520 | | | | | 525 | | | |
| Asn | Arg | Lys | Glu | Ile | Gln | Asp | Ser | Gln | Val | Pro | Leu | Glu | Lys | Glu | Thr |
| | 530 | | | | | 535 | | | | | 540 | | | | |
| Leu | Lys | Ser | Leu | Gly | Glu | Glu | Ile | Gln | Glu | Ser | Leu | Lys | Thr | Leu | Glu |
| 545 | | | | | 550 | | | | | 555 | | | | | 560 |
| Asn | Gln | Ser | His | Glu | Thr | Leu | Glu | Arg | Glu | Asn | Gln | Glu | Cys | Pro | Arg |
| | | | | 565 | | | | | 570 | | | | | 575 | |
| Ser | Leu | Glu | Glu | Asp | Leu | Glu | Thr | Leu | Lys | Ser | Leu | Glu | Lys | Glu | Asn |
| | | | | 580 | | | | | 585 | | | | | 590 | |
| Lys | Arg | Ala | Ile | Lys | Gly | Cys | Gly | Gly | Ser | Glu | Thr | Ser | Arg | Lys | Arg |
| | | 595 | | | | | 600 | | | | | 605 | | | |
| Gly | Cys | Arg | Gln | Leu | Lys | Pro | Thr | Gly | Lys | Glu | Asp | Thr | Gln | Thr | Leu |
| | 610 | | | | | 615 | | | | | 620 | | | | |
| Gln | Ser | Leu | Gln | Lys | Glu | Asn | Gln | Glu | Leu | Met | Lys | Ser | Leu | Glu | Gly |
| 625 | | | | | 630 | | | | | 635 | | | | | 640 |

```
Asn Leu Glu Thr Phe Leu Phe Pro Gly Thr Glu Asn Gln Glu Leu Val
                645                 650                 655

Ser Ser Leu Gln Glu Asn Leu Glu Ser Leu Thr Ala Leu Glu Lys Glu
            660                 665                 670

Asn Gln Glu Pro Leu Arg Ser Pro Glu Val Gly Asp Glu Glu Ala Leu
        675                 680                 685

Arg Pro Leu Thr Lys Glu Asn Gln Glu Pro Leu Arg Ser Leu Glu Asp
    690                 695                 700

Glu Asn Lys Glu Ala Phe Arg Ser Leu Glu Lys Glu Asn Gln Glu Pro
705                 710                 715                 720

Leu Lys Thr Leu Glu Glu Asp Gln Ser Ile Val Arg Pro Leu Glu
                725                 730                 735

Thr Glu Asn His Lys Ser Leu Arg Ser Leu Glu Glu Gln Asp Gln Glu
            740                 745                 750

Thr Leu Arg Thr Leu Glu Lys Glu Thr Gln Gln Arg Arg Arg Ser Leu
        755                 760                 765

Gly Glu Gln Asp Gln Met Thr Leu Arg Pro Pro Glu Lys Val Asp Leu
770                 775                 780

Glu Pro Leu Lys Ser Leu Asp Gln Glu Ile Ala Arg Pro Leu Glu Asn
785                 790                 795                 800

Glu Asn Gln Glu Phe Leu Lys Ser Leu Lys Glu Glu Ser Val Glu Ala
                805                 810                 815

Val Lys Ser Leu Glu Thr Glu Ile Leu Glu Ser Leu Lys Ser Ala Gly
            820                 825                 830

Gln Glu Asn Leu Glu Thr Leu Lys Ser Pro Glu Thr Gln Ala Pro Leu
            835                 840                 845

Trp Thr Pro Glu Glu Ile Asn Lys Ser Gly Gly Asn Glu Ser Ser Arg
    850                 855                 860

Lys Gly Asn Ser Arg Thr Thr Gly Val Cys Gly Ser Glu Pro Arg Asp
865                 870                 875                 880

Ile Gln Thr Pro Gly Arg Gly Glu Ser Gly Ile Ile Glu Ile Ser Gly
                885                 890                 895

Ser Met Glu Pro Gly Glu Phe Glu Ile Ser Arg Gly Val Asp Lys Glu
            900                 905                 910

Ser Gln Arg Asn Leu Glu Glu Glu Asn Leu Gly Lys Gly Glu Tyr
        915                 920                 925

Gln Glu Ser Leu Arg Ser Leu Glu Glu Glu Gly Gln Glu Leu Pro Gln
930                 935                 940

Ser Ala Asp Val Gln Arg Trp Glu Asp Thr Val Glu Lys Asp Gln Glu
945                 950                 955                 960

Leu Ala Gln Glu Ser Pro Pro Gly Met Ala Gly Val Glu Asn Lys Asp
            965                 970                 975

Glu Ala Glu Leu Asn Leu Arg Glu Gln Asp Gly Phe Thr Gly Lys Glu
        980                 985                 990

Glu Val Val Gln Gln Gly Glu Leu Asn Ala Thr Glu Glu Val Trp Phe
    995                 1000                1005

Pro Gly Glu Gly His Pro Glu Asn Pro Glu Pro Lys Glu Gln Arg Gly
    1010                1015                1020

Leu Val Glu Gly Ala Ser Val Lys Gly Gly Ala Glu Gly Leu Gln Asp
1025                1030                1035                1040

Pro Glu Gly Gln Ser Gln Gln Val Gly Thr Pro Gly Leu Gln Ala Pro
                1045                1050                1055

Gln Gly Leu Pro Glu Ala Ile Glu Pro Leu Val Glu Asp Asp Val Ala
            1060                1065                1070

Pro Gly Gly Asp Gln Ala Ser Pro Glu Val Met Leu Gly Ser Glu Pro
```

```
        1075              1080                    1085
Ala Met Gly Glu Ser Ala Ala Gly Ala Glu Pro Gly Leu Gly Gln Gly
    1090              1095                    1100
Val Gly Gly Leu Gly Asp Pro Gly His Leu Thr Arg Glu Glu Val Met
1105              1110                    1115                   1120
Glu Pro Pro Leu Glu Glu Glu Ser Leu Glu Ala Lys Arg Val Gln Gly
                1125                    1130                   1135
Leu Glu Gly Pro Arg Lys Asp Leu Glu Glu Ala Gly Gly Leu Gly Thr
                1140                    1145                   1150
Glu Phe Ser Glu Leu Pro Gly Lys Ser Arg Asp Pro Trp Glu Pro Pro
                1155                    1160                   1165
Arg Glu Gly Arg Glu Glu Ser Glu Ala Glu Ala Pro Arg Gly Ala Glu
                1170                    1175                   1180
Glu Ala Phe Pro Ala Glu Thr Leu Gly His Thr Gly Ser Asp Ala Pro
1185                    1190                    1195                   1200
Ser Pro Trp Pro Leu Gly Ser Glu Glu Ala Glu Glu Asp Val Pro Pro
                1205                    1210                   1215
Val Leu Val Ser Pro Ser Pro Thr Tyr Thr Pro Ile Leu Glu Asp Ala
                1220                    1225                   1230
Pro Gly Leu Gln Pro Gln Ala Glu Gly Ser Gln Glu Ala Ser Trp Gly
                1235                    1240                   1245
Val Gln Gly Arg Ala Glu Ala Gly Lys Val Glu Ser Glu Gln Glu Glu
                1250                    1255                   1260
Leu Gly Ser Gly Glu Ile Pro Glu Gly Leu Gln Glu Glu Gly Glu Glu
1265                    1270                    1275                   1280
Ser Arg Glu Glu Ser Glu Glu Asp Glu Leu Gly Glu Thr Leu Pro Asp
                1285                    1290                   1295
Ser Thr Pro Leu Gly Phe Tyr Leu Arg Ser Pro Thr Ser Pro Arg Trp
                1300                    1305                   1310
Thr Pro Leu Glu Ser Arg Gly His Pro Leu Lys Glu Thr Gly Lys Glu
                1315                    1320                   1325
Gly Trp Asp Pro Ala Val Leu Ala Ser Glu Gly Leu Glu Glu Pro Ser
                1330                    1335                   1340
Glu Lys Glu Glu Gly Glu Glu Gly Glu Glu Glu Cys Gly Arg Asp Ser
1345                    1350                    1355                   1360
Asp Leu Ser Glu Glu Phe Glu Asp Leu Gly Thr Glu Ala Pro Phe Leu
                1365                    1370                   1375
Pro Gly Val Pro Gly Glu Val Ala Glu Pro Leu Gly Gln Val Pro Gln
                1380                    1385                   1390
Leu Leu Leu Asp Pro Ala Ala Trp Asp Arg Asp Gly Glu Ser Asp Gly
                1395                    1400                   1405
Phe Ala Asp Glu Glu Glu Ser Gly Glu Glu Gly Glu Glu Asp Gln Glu
                1410                    1415                   1420
Glu Gly Arg Glu Pro Gly Ala Gly Arg Trp Gly Pro Gly Ser Ser Val
1425                    1430                    1435                   1440
Gly Ser Leu Gln Ala Leu Ser Ser Ser Gln Arg Gly Glu Phe Leu Glu
                1445                    1450                   1455
Ser Asp Ser Val Ser Val Ser Val Pro Trp Asp Asp Ser Leu Arg Gly
                1460                    1465                   1470
Ala Val Ala Gly Ala Pro Lys Thr Ala Leu Glu Thr Glu Ser Gln Asp
                1475                    1480                   1485
Ser Ala Glu Pro Ser Gly Ser Glu Glu Glu Ser Asp Pro Val Ser Leu
                1490                    1495                   1500
Glu Arg Glu Asp Lys Val Pro Gly Pro Leu Glu Ile Pro Ser Gly Met
1505                    1510                    1515                   1520
```

Glu Asp Ala Gly Pro Gly Ala Asp Ile Ile Gly Val Asn Gly Gln Gly
                1525                    1530                1535

Pro Asn Leu Glu Gly Lys Ser Gln His Val Asn Gly Gly Val Met Asn
            1540                1545                1550

Gly Leu Glu Gln Ser Glu Glu Ser Gly Ala Arg Asn Ala Leu Val Ser
        1555                1560                1565

Glu Gly Asp Arg Gly Ser Pro Phe Gln Glu Glu Glu Gly Ser Ala Leu
    1570                1575                1580

Lys Arg Ser Ser Ala Gly Ala Pro Val His Leu Gly Gln Gly Gln Phe
1585                1590                1595                1600

Leu Lys Phe Thr Gln Arg Glu Gly Asp Arg Glu Ser Trp Ser Ser Gly
                1605                1610                1615

Glu Asp